United States Patent
Harada et al.

(10) Patent No.: US 7,262,321 B2
(45) Date of Patent: Aug. 28, 2007

(54) SALT SUITABLE FOR AN ACID GENERATOR AND A CHEMICALLY AMPLIFIED RESIST COMPOSITION CONTAINING THE SAME

(75) Inventors: Yukako Harada, Settu (JP); Isao Yoshida, Ikeda (JP); Yoshiyuki Takata, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/516,644

(22) Filed: Sep. 7, 2006

(65) Prior Publication Data

US 2007/0100096 A1 May 3, 2007

(30) Foreign Application Priority Data

Oct. 28, 2005 (JP) .............................. 2005-314037

(51) Int. Cl.
*C07C 69/00* (2006.01)
(52) U.S. Cl. .......................... 560/129; 560/1; 560/150; 430/270.1
(58) Field of Classification Search .................... 560/1, 560/129, 150; 430/270.1
See application file for complete search history.

(56) References Cited

U.S. PATENT DOCUMENTS

2003/0194639 A1 10/2003 Miya et al.
2006/0194982 A1 8/2006 Harada et al.

FOREIGN PATENT DOCUMENTS

DE DD 295421 * 10/1991

JP 2004-117959 A 4/2004

* cited by examiner

Primary Examiner—Thurman K. Page
Assistant Examiner—Sudhakar Katakam
(74) Attorney, Agent, or Firm—Birch, Stewart, Kolasch & Birch, LLP

(57) ABSTRACT

The present invention provides a salt of the formula (I):

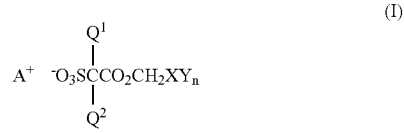

wherein X represents divalent or trivalent residue of acyclic hydrocarbon having 1 to 30 carbon atoms or divalent or trivalent residue of hydrocarbon having 3 to 30 carbon atoms which contains monocyclic or bicyclic ring, wherein —$CH_2$— in the hydrocarbon may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ each independently represent fluorine atom or perfluoroalkyl group having 1 to 6 carbon atoms; $A^+$ represents organic counter ion; Y represents hydroxyl group, cyano group or methoxy group; and n shows 1 or 2.

The present invention also provides a chemically amplified resist composition comprising the salt of the formula (I).

25 Claims, No Drawings

SALT SUITABLE FOR AN ACID GENERATOR AND A CHEMICALLY AMPLIFIED RESIST COMPOSITION CONTAINING THE SAME

This nonprovisional application claims priority under 35 U.S.C. §119(a) on Patent Application No. 2005-314037 filed in JAPAN on Oct. 28, 2005, the entire contents of which are hereby incorporated by reference.

FIELD OF THE INVENTION

The present invention relates to a salt suitable for an acid generator used for a chemical amplification type resist which is used in fine processing of semiconductors, and a chemically amplified resist composition containing the salt.

BACKGROUND OF THE INVENTION

A chemically amplified resist composition used for semiconductor microfabrication employing a lithography process contains an acid generator comprising a compound generating an acid by irradiation.

In semiconductor microfabrication, it is desirable to form patterns having high resolution and, and it is expected for a chemically amplified resist composition to give such patterns.

Recently, a chemically amplified resist composition containing triphenylsulfonium 1-adamantanemethoxycarbonyldifluoromethansulfonate, p-tolyldiphenylsulfonium perfluorooctanesulfonate, and the like are proposed (e.g. JP2004-4561-A), and a salt providing a chemically amplified resist composition giving patterns having higher resolution.

SUMMARY OF THE INVENTION

Objects of the present invention are to provide a salt suitable for an acid generator capable of providing chemically amplified resist compositions giving patterns having better resolution and to provide a process for producing the salt.

Another objects of the present invention are to provide synthetic intermediates for the salts and to provide a process for producing the synthetic intermediates or the salts.

Still another object of the present invention are to provide a chemically amplified resist composition containing the salts.

These and other objects of the present invention will be apparent from the following description.

The present invention relates to the followings:

<1> A salt of the formula (I):

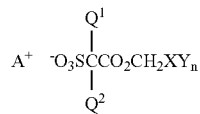
(I)

wherein X represents divalent or trivalent residue of acyclic hydrocarbon having 1 to 30 carbon atoms or divalent or trivalent residue of hydrocarbon having 3 to 30 carbon atoms which contains monocyclic or bicyclic ring, wherein $-CH_2-$ in the hydrocarbon may be substituted with $-O-$ and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ each independently represent fluorine atom or perfluoroalkyl group having 1 to 6 carbon atoms; $A^+$ represents organic counter ion; Y represents hydroxyl group, cyano group or methoxy group; and n shows 1 or 2. Hereinafter, the salt of the formula (I) is also referred to as Salt (I).

<2> The salt according to <1>, wherein X is divalent or trivalent residue of alkane having 1 to 30 carbon atoms, or divalent or trivalent residue of monocyclic hydrocarbon or of bicyclic hydrocarbon having 3 to 30 carbon atoms, wherein $-CH_2-$ in the alkane may be substituted with $-O-$ and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group.

<3> The salt according to <2>, wherein the divalent or trivalent residue of monocyclic or bicyclic hydrocarbon in X is divalent or trivalent residue of monocycloalkane or bicycloalkane.

<4> The salt according to any of <1> to <3>, wherein $A^+$ is at least one cation selected from the group consisting of the formula (IIe), the formula (IIb), the formula (IIc) and the formula (IId):

a cation of the formula (IIe):

(IIe)

wherein $P^{25}$, $P^{26}$ and $P^{27}$ each independently represent alkyl group having 1 to 30 carbon atoms or cyclic hydrocarbon group having 3 to 30 carbon atoms, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms, a cation of the formula (IIb):

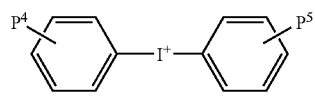
(IIb)

wherein $P^4$ and $P^5$ each independently represent hydrogen atom, hydroxyl group, alkyl group having 1 to 12 carbon atoms or alkoxy group having 1 to 12 carbon atoms, a cation of the formula (IIc):

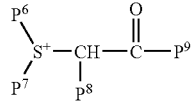

wherein $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent $S^+$, and one or more —$CH_2$— in the divalent acyclic hydrocarbon group is optionally substituted with —CO—, —O— or —S—, $P^8$ represents hydrogen, $P^9$ represents alkyl having 1 to 12 carbon atoms, cycloalkyl having 3 to 12 carbon atoms or aromatic ring group optionally substituted, or $P^8$ and $P^9$ bond to form divalent acyclic hydrocarbon group which forms 2-oxocycloalkyl together with the adjacent —CHCO—, and one or more —$CH_2$— in the divalent acyclic hydrocarbon group is optionally substituted with —CO—, —O— or —S—, a cation of the formula (IId):

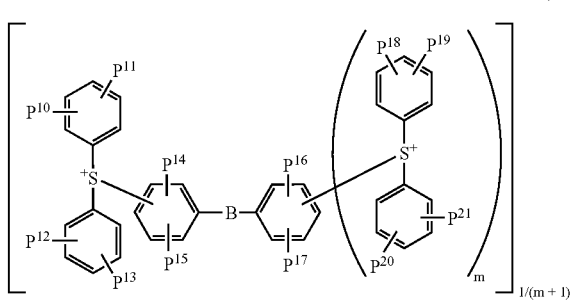

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen atom, hydroxyl group, alkyl group having 1 to 12 carbon atoms or alkoxy group having 1 to 12 carbon atoms, B represents sulfur atom or oxygen atom, and m shows 0 or 1.

<5> The salt according to <4>, wherein the cation of the formula (IIe) is a cation of the formula (IIf), (IIg) or (IIh):

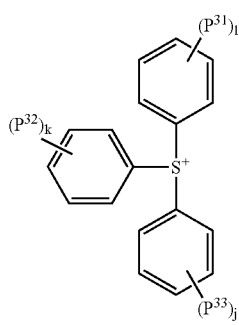

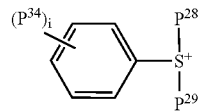

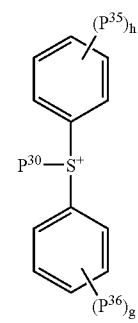

wherein $P^{28}$, $P^{29}$ and $P^{30}$ each independently represent alkyl group having 1 to 20 carbon atoms or cyclic hydrocarbon group having 3 to 30 except phenyl group, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms; and $P^{31}$, $P^{32}$ $P^{33}$, $P^{34}$, $P^{35}$ and $P^{36}$ each independently represent hydoxyl group, alkyl group having 1 to 12 carbon atoms, alkoxy group having 1 to 12 carbon atoms or cyclic hydrocarbon group having 3 to 12 carbon atoms, and l, k, j, i, h and g each independently show an integer of 0 to 5.

<6> The salt according to <4>, wherein the cation of the formula (IIe) is a cation of the formula (IIa):

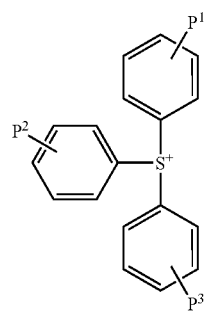

wherein $P^1$, $P^2$ and $P^3$ each independently represent hydrogen atom, hydroxyl group, alkyl group having 1 to 12 carbon atoms or alkoxy group having 1 to 12 carbon atoms.

<7> The salt according to <6>, wherein the cation of the formula (IIa) is a cation of the formula (IIIe):

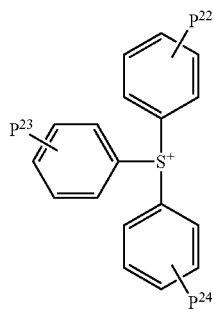

wherein $P^{22}$, $P^{23}$ and $P^{24}$ each independently represent hydrogen atom or alkyl group having 1 to 4 atoms.

<8> The salt according to any of <1> to <7>, wherein each of $Q^1$ and $Q^2$ is independently fluorine atom or trifluoromethyl group.

<9> The salt according to any of <2> to <8>, wherein X is divalent or trivalent residue of alkane having 1 to 30 carbon atoms, of cycloalkane having 3 to 10 carbon atoms or of norbornane, wherein —$CH_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ are both fluorine atoms; Y is hydroxyl group; and n shows 1.

<10> The salt according to <1>, wherein the salt is the one of the formula (IIIa), (IIIb) or (IIIc);

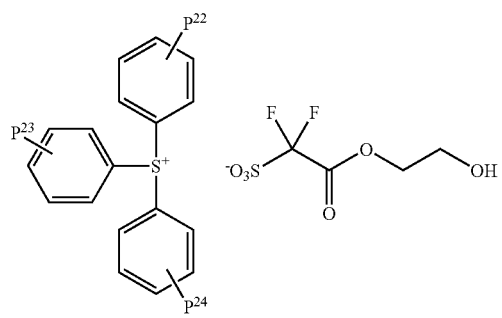

(IIIa)

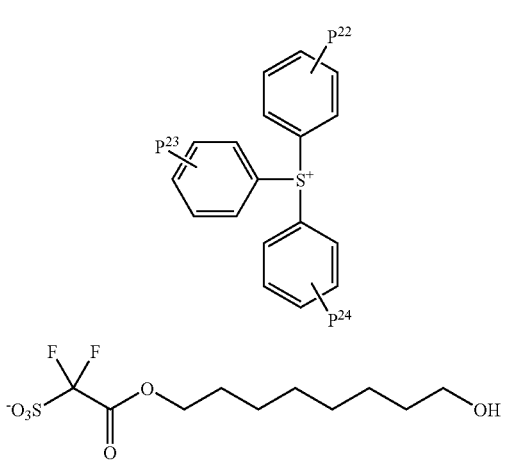

(IIIb)

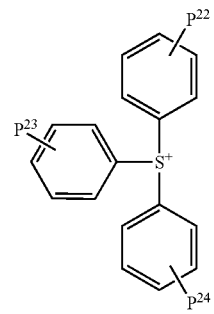

(IIIc)

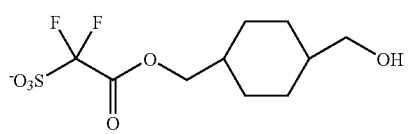

wherein $P^{22}$, $P^{23}$ and $P^{24}$ have the same meanings as defined above.

<11> An ester compound of the formula (IV)

(IV)

wherein M represents Li, Na, K or Ag, $Q^1$, $Q^2$, Y and n have the same meanings as defined above.

<12> The composition according to <11>, wherein each of $Q^1$ and $Q^2$ is independently fluorine atom or trifluoromethyl group.

<13> A process for producing an ester compound of the formula (IV), which comprises reacting an alcohol compound of the formula (V)

$$HOCH_2XY_n \quad (V)$$

wherein X, Y and n have the same meanings as defined above, with a carboxylic acid compound of the formula (VI)

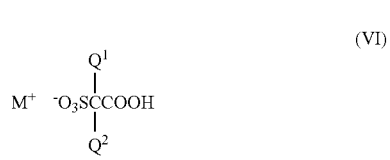

(VI)

wherein M, $Q^1$ and $Q^2$ have the same meanings as defined above.

<14> A process for producing Salt (I), which comprises reacting an ester compound of the formula (IV) with a compound of the formula (VII)

$$A^+Z^- \quad (VII)$$

wherein Z represents F, Cl, Br, I, $BF_4$, $AsF_6$, $PF_6$ or $ClO_4$, and $A^+$ has the same meaning as defined above.

<15> A chemically amplified resist composition comprising Salt (I), and a resin which contains a structural unit having an acid-labile group and which itself is insoluble or poorly soluble in an alkali aqueous solution but becomes soluble in an alkali aqueous solution by the action of an acid.

<16> The composition according to <15>, wherein each of $Q^1$ and $Q^2$ is independently fluorine atom or trifluoromethyl group.

<17> The composition according to <15> or <16>, wherein the resin contains a structural unit derived from a monomer having a bulky and acid-labile group.

<18> The composition according to <17>, wherein the bulky and acid-labile group is 2-alkyl-2-adamantyl group or 1-(1-adamantyl)-1-alkylalkyl group.

<19> The composition according to <17>, wherein the monomer having bulky and acid-labile group is 2-alkyl-2-adamantyl (meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

<20> The composition according to any of <15> to <19>, wherein the composition further comprises a basic compound.

<21> The composition according to any of <15> to <20>, wherein X is divalent or trivalent residue of alkane having 1 to 30 carbon atoms, or divalent or trivalent residue of monocyclic hydrocarbon or of bicyclic hydrocarbon having 3 to 30 carbon atoms, wherein —$CH_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group.

<22> The composition according to <21>, wherein the divalent or trivalent residue of monocyclic or bicyclic hydrocarbon in X is divalent or trivalent residue of monocycloalkane or bicycloalkane.

<23> The composition according to any of <15> to <22>, wherein $A^+$ is at least one cation selected from the group consisting of the formula (IIe), the formula (IIb), the formula (IIc) and the formula (IId).

<24> The composition according to <23>, wherein the cation of the formula (IIe) is a cation of the formula (IIf), (IIg) or (IIh).

<25> The composition according to <23>, wherein the cation of the formula (IIe) is a cation of the formula (IIa).

<26> The composition according to <25>, wherein the cation of the formula (IIa) is a cation of the formula (IIIe)

<27> The composition according to <21>, wherein X is divalent or trivalent residue of alkane having 1 to 30 carbon atoms, of cycloalkane having 3 to 10 carbon atoms or of norbornane, wherein —$CH_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ are both fluorine atoms; Y is hydroxyl group; and n shows 1.

<28> The composition according to any of <15> to <20>, wherein the salt is the one of the formula (IIIa), (IIIb) or (IIIc).

DESCRIPTION OF PREFERRED EMBODIMENTS

The present invention provides Salt (I).

X in the formulae (I), (IV) and (V) represents divalent or trivalent residue of acyclic hydrocarbon having 1 to 30 carbon atoms or divalent or trivalent residue of hydrocarbon having 3 to 30 carbon atoms which contains monocyclic or bicyclic ring. The —$CH_2$— in the hydrocarbon may be substituted with —O—. One or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group.

It is preferred that X is divalent or trivalent residue of alkane having 1 to 30 carbon atoms, or divalent or trivalent residue of monocyclic hydrocarbon or of bicyclic hydrocarbon having 3 to 30 carbon atoms, wherein —$CH_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group. The alkane may be linear or branched. As the monocyclic hydrocarbon, monocycloalkane is preferred, and the monocycloalkane is also simply referred to as cycloalkane. As the bicyclic hydorcarbon, bicycloalkane is preferred.

Examples of X include

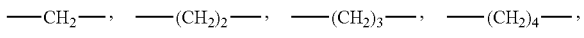
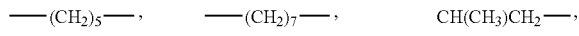
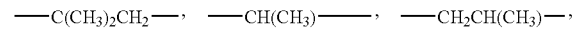
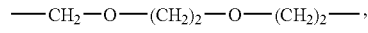
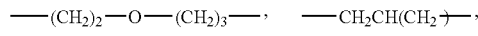
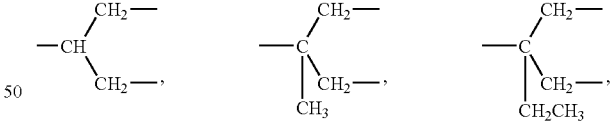
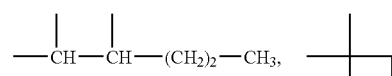
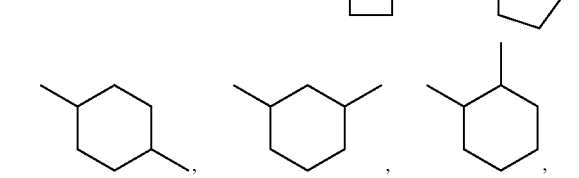
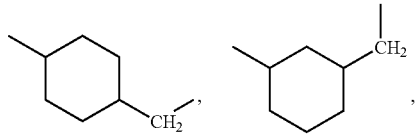

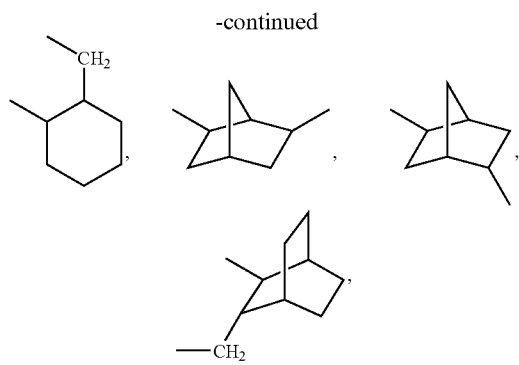

and the like. In each of the formulae above, a straight line with an open end shows a bond which is extended from an adjacent carbon atom and which does not specifies a group to be bonded but should bond to —CH$_2$— or Y in the formula (I), (IV) or (V).

In X, the divalent or trivalent residue of alkane having 1 to 30 carbon atoms, the divalent or trivalent residue of cycloalkane having 3 to 30 carbon atoms and the divalent or trivalent residue of norbornane are more preferred. The —CH$_2$— in the alkane or cycloalkane may be substituted with —O—, and one or more hydrogen atom in the alkane, cycloalkane and norbornane is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group. The cycloalkane preferably has 3 to 10 carbon atoms.

Y represents hydroxyl group, cyano group or methoxy group and n, number of Y, is 1 or 2. When n is 1, X is divalent group, and when n is 2, X is trivalent group. It is preferred that Y is hydroxyl group and n is 1.

Q$^1$ and Q$^2$ each independently represent fluorine atom or perfluoroalkyl group having 1 to 6 carbon atoms such as trifluoromethyl group, pentafluoroethyl group, heptafluoropropyl group, nonafluorobutyl group, undecafluoropentyl group, tridecafluorohexyl group, and the like. As Q$^1$ and Q$^2$, fluorine atom and trifluoromethyl group are preferred.

Specific examples of anion part of the Salt (I) include the followings:

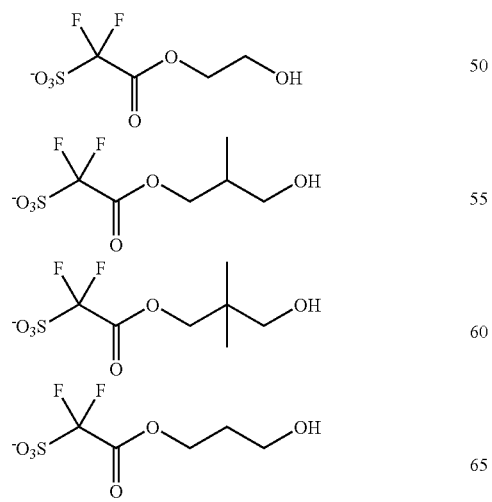

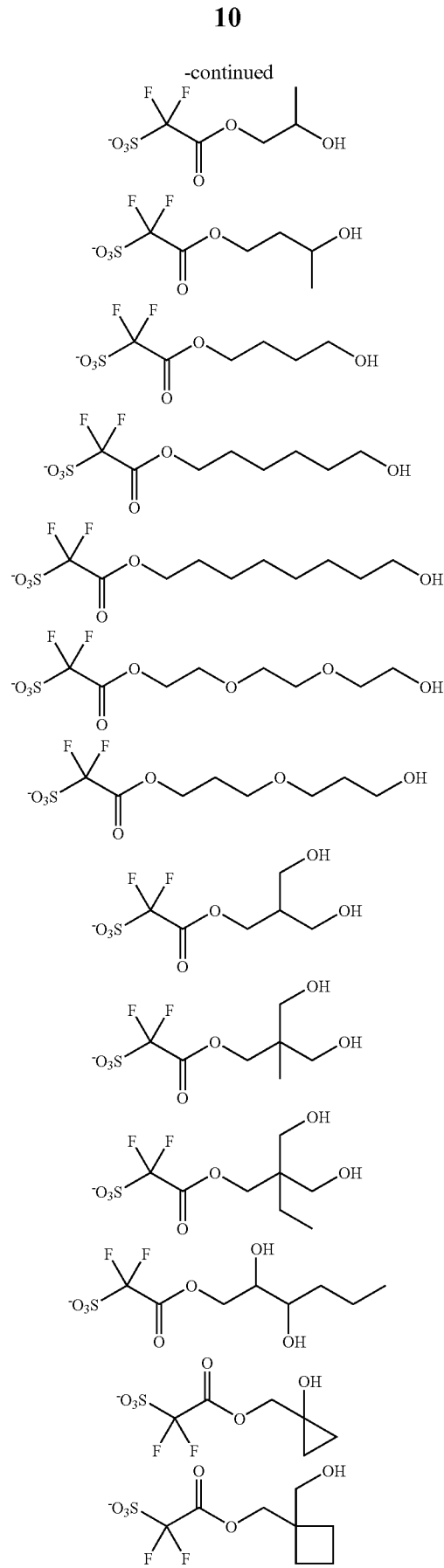

-continued
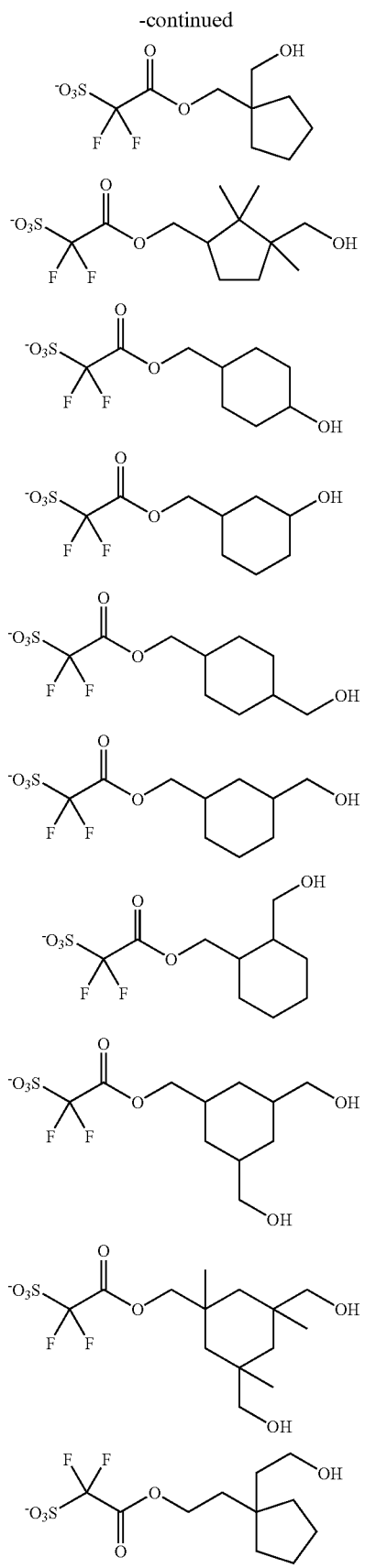
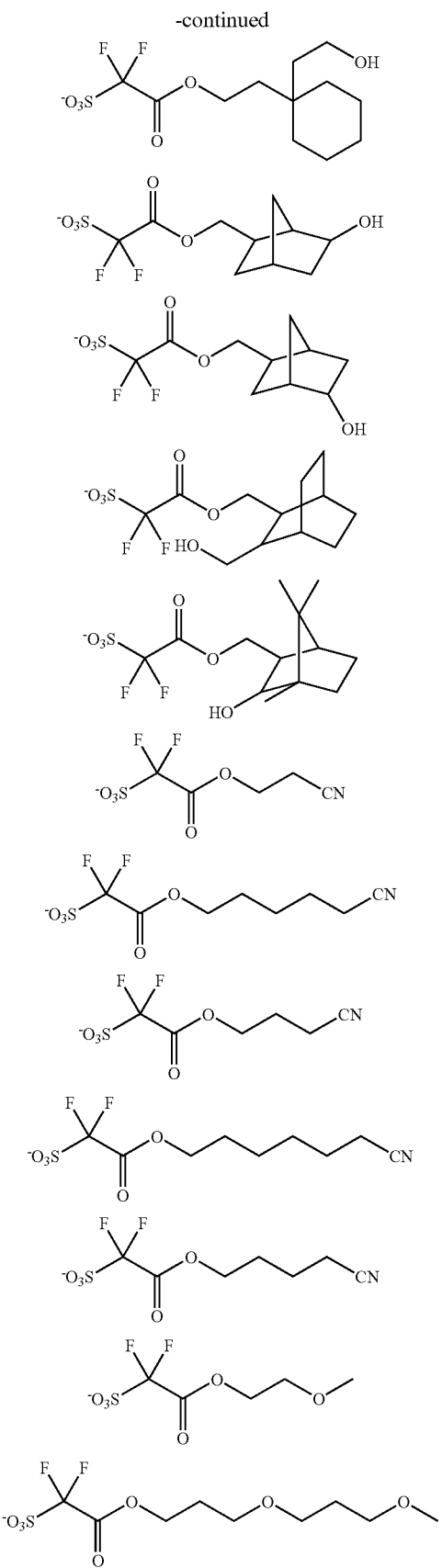

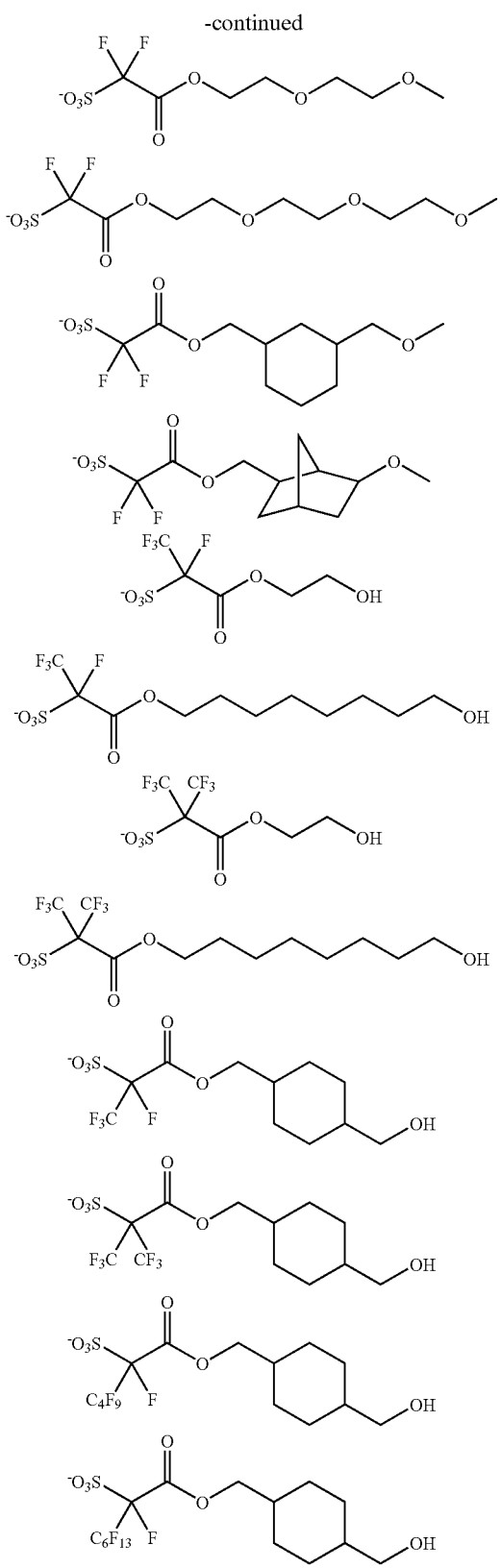

A⁺ in the formulae (I) and (VII) represents organic counter ion. Examples thereof include the cations of the formulae (IIe), (IIb), (IIc) and (IId).

In the cation of the formula (IIe), $P^{25}$, $P^{26}$ and $P^{27}$ each independently represent alkyl group having 1 to 30 carbon atoms or cyclic hydrocarbon group having 3 to 30 carbon atoms. One or more hydrogen atom in the alkyl group in the formula (IIe) is optionally substituted with hydroxyl group, alkoxy group having 1 to 12 carbon atoms or cyclic hydrocarbon group having 3 to 12 carbon atoms and one or more hydrogen atom in the cyclic hydrocarbon group in the formula (IIe) is optionally substituted with hydroxyl group, alkyl group having 1 to 12 carbon atoms or alkoxy group having 1 to 12 carbon atoms.

Examples of the alkyl group in the formula (IIe) include methyl group, ethyl group, propyl group, isopropyl group, n-butyl group, sec-butyl group, tert-butyl group, pentyl group, hexyl group, octyl group, 2-ethylhexyl group, and the like, and examples of the alkoxy group include methoxy group, ethoxy group, propoxy group, butoxy group, hexyloxy group, octyloxy group, 2-ethylhexyloxy group, and the like. Examples of the cyclic hydrocarbon group include cyclopentyl group, cyclohexyl group, adamantyl group, bicyclohexyl group, phenyl group, naphtyl group, fluorenyl group, biphenyl group, and the like.

In the cation of the formula (IIe), cations of the formulae (IIf), (IIg) and (IIh) are preferred. In the cations of the formulae (IIf), (IIg) and (IIh), $P^{28}$, $P^{29}$ and $P^{30}$ each independently represent alkyl group having 1 to 20 carbon atoms or cyclic hydrocarbon group having 3 to 30 except phenyl group. One or more hydrogen atom in the alkyl group in the formulae (IIf), (IIg) and (IIh) is optionally substituted with hydroxyl group, alkoxy group having 1 to 12 carbon atoms or cyclic hydrocarbon group having 3 to 12 carbon atoms. One or more hydrogen atom in the cyclic hydrocarbon group in the formulae (IIf), (IIg) and (IIh) is optionally substituted with hydroxyl group, alkyl group having 1 to 12 carbon atoms or alkoxy group having 1 to 12 carbon atoms. Examples of the alkyl group, alkoxy group and cyclic hydrocarbon group include the same groups as mentioned in the formula (IIe) above.

$P^{31}$, $P^{32}$, $P^{33}$, $P^{34}$, $P^{35}$ and $P^{36}$ each independently represent hydoxyl group, alkyl group having 1 to 12 carbon atoms, alkoxy group having 1 to 12 carbon atoms or cyclic hydrocarbon group having 3 to 12 carbon atoms, and l, k, j, i, h and g each independently show an integer of 0 to 5. Examples of the alkyl group, alkoxy group and cyclic hydrocarbon group include the sane groups as mentioned in the formula (IIe) above.

In the cation of the formula (IIe), the one of the formula (IIa) is more preferred. In the cation of the formula (IIa), $P^1$, $P^2$ and $P^3$ each independently represent hydrogen atom, hydroxyl group, alkyl group having 1 to 12 carbon atoms or alkoxy group having 1 to 12 carbon atoms.

Examples of the alkyl group and alkoxy group in the formula (IIa) include the same groups as mentioned in the formula (IIe) above.

In the cation of the formula (IIa), the one of the formula (IIIe) above is preferred for the easiness of production.

In the cation of the formula (IIb), $P^4$ and $P^5$ each independently represent hydrogen atom, hydroxyl group, alkyl group having 1 to 12 carbon atoms or alkoxy group having 1 to 12 carbon atoms. Examples of the alkyl group and alkoxy group include the same groups as mentioned in the formula (IIe) above.

In the cation of the formula (IIc), $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent S+, and at least one —CH$_2$— in the divalent acyclic hydrocarbon may be substituted with —CO—, —O— or —S—.

P$^8$ represents hydrogen, P$^9$ represents alkyl having 1 to 12 carbon atoms, cycloalkyl having 3 to 12 carbon atoms or aromatic ring group optionally substituted, or P$^8$ and P$^9$ bond to form divalent acyclic hydrocarbon group which forms 2-oxocycloalkyl together with the adjacent —CHCO—, and one or more —CH$_2$— in the divalent acyclic hydrocarbon group is optionally substituted with —CO—, —O— or —S—.

In P$^6$, P$^7$ and P$^9$, specific examples of the alkyl group include methyl group, ethyl group, propyl group, isopropyl group, butyl group, tert-butyl group, pentyl group, hexyl group, and the like, and specific examples of the cycloalkyl group include cyclopropyl group, cyclobutyl group, cyclopentyl group, cyclohexyl group, cycloheptyl group, cyclodecyl group, and the like. Specific examples of the divalent acyclic hydrocarbon group having 3 to 12 carbon atoms formed by bonding P$^6$ and P$^7$ include trimethylene group, tetramethylene group, pentamethylene group, and the like, and specific examples of the ring group formed by adjacent S+ and divalent acyclic hydrocarbon group by P$^6$ and P$^7$ include pentamethylenesulfonio group, tetramethylenesulfonio group, oxybisethylenesulfonio group, and the like. In P$^9$, specific examples of the aromatic ring group include phenyl, tolyl, xylyl, naphtyl and the like. Specific examples of the divalent acyclic hydrocarbon group formed by bonding P$^8$ and P$^9$ include methylene group, ethylene group, trimethylene group, tetramethylene group, pentamethylene group, and the like, and specific examples of the 2-oxocycloalkyl formed by bonding P$^8$ and P$^9$ together with the adjacent —CHCO— include 2-oxocyclohexyl, 2-oxocyclopentyl and the like.

In the cation of the formula (IId), P$^{10}$, P$^{11}$, P$^{12}$, P$^{13}$, P$^{14}$, P$^{15}$, P$^{16}$, P$^{17}$, P$^{18}$, P$^{19}$, P$^{20}$ and P$^{21}$ each independently represent hydrogen atom, hydroxyl group, alkyl group having 1 to 12 carbon atoms or alkoxy group having 1 to 12 carbon atoms, B represents sulfur atom or oxygen atom, and m represents 0 or 1. Examples of the alkyl group and alkoxy group include the same groups as mentioned in the formula (IIe) above.

Specific examples of the cation of the formula (IIe) include the following:

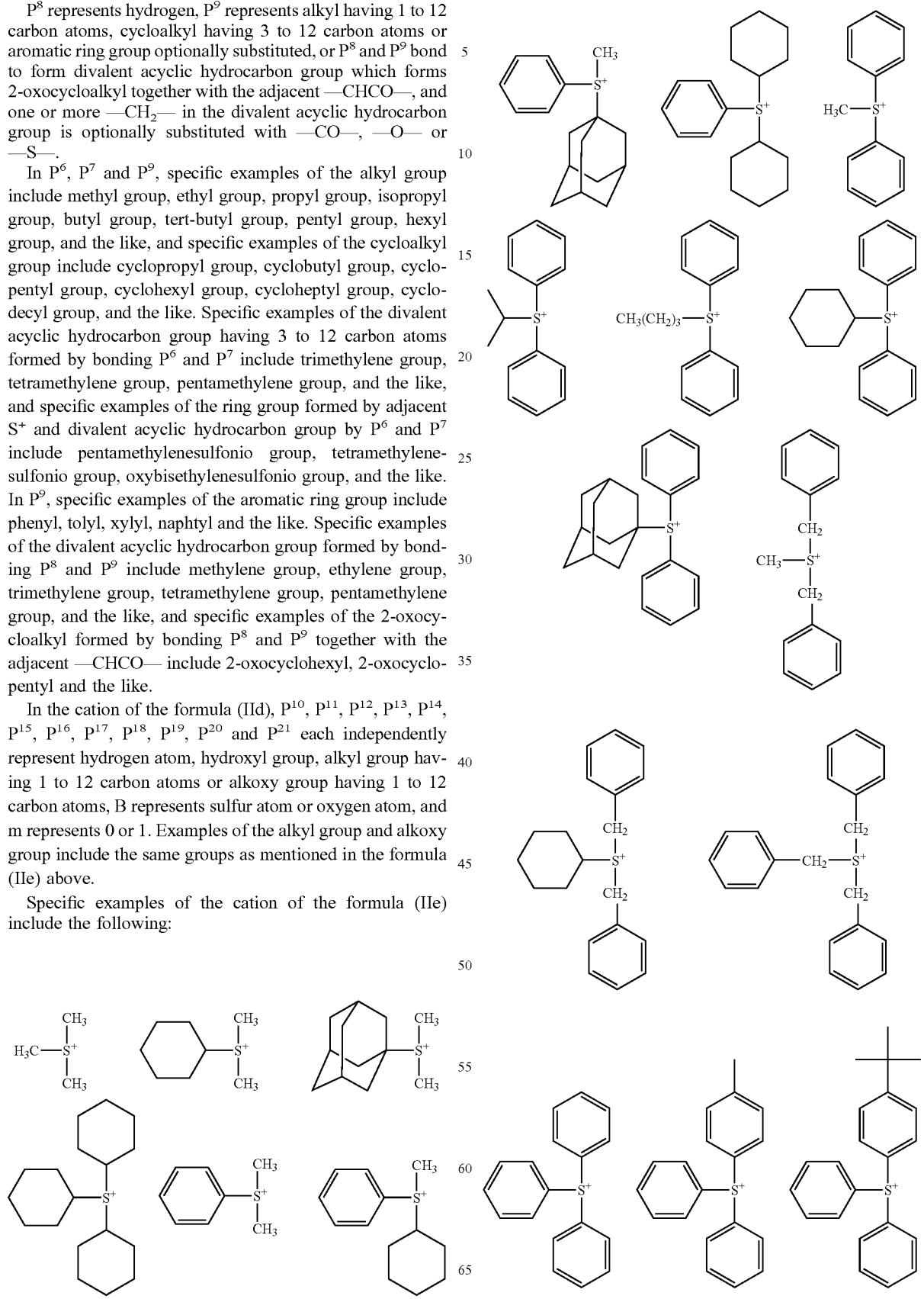

-continued

-continued
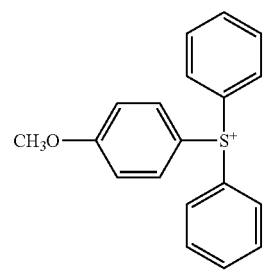
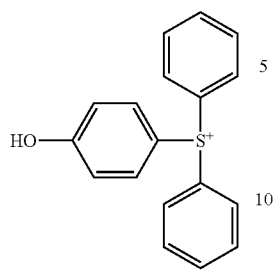
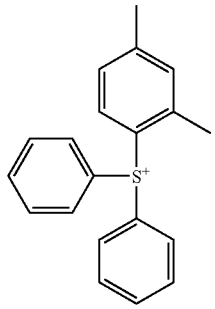
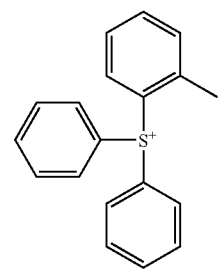
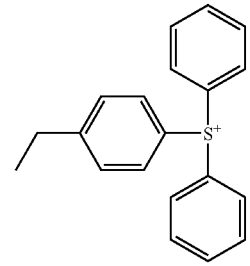
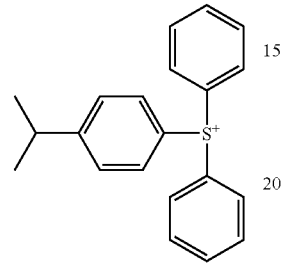
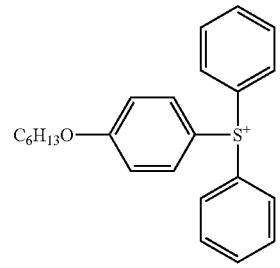
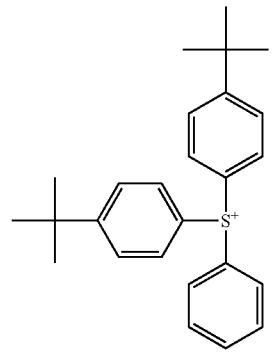
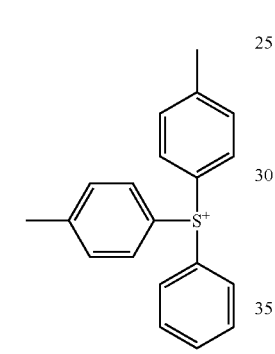
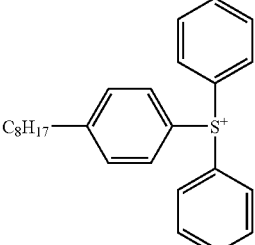
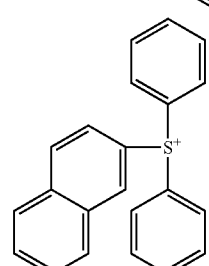
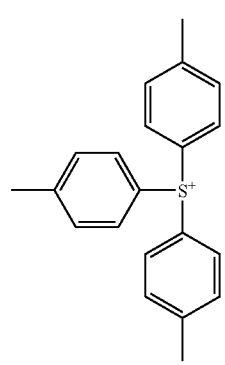
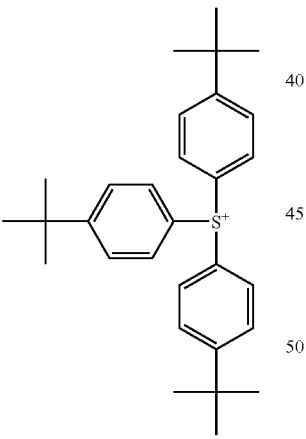
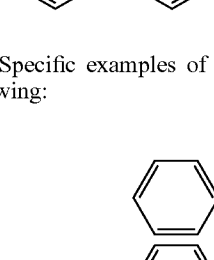
Specific examples of the formula (IIb) include the following:
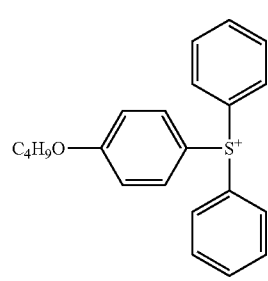
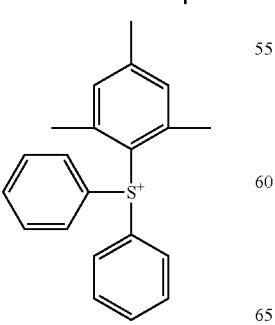
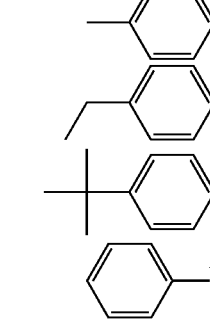
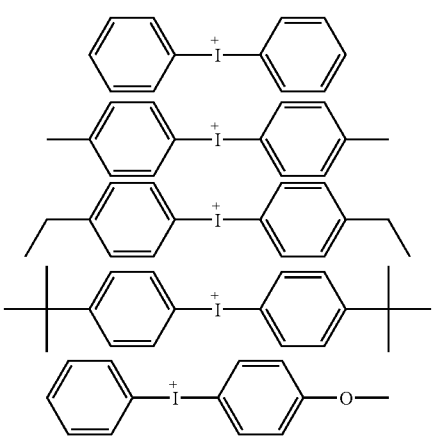

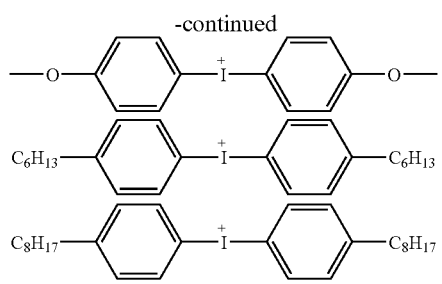
Specific examples of the formula (IIc) include the following:
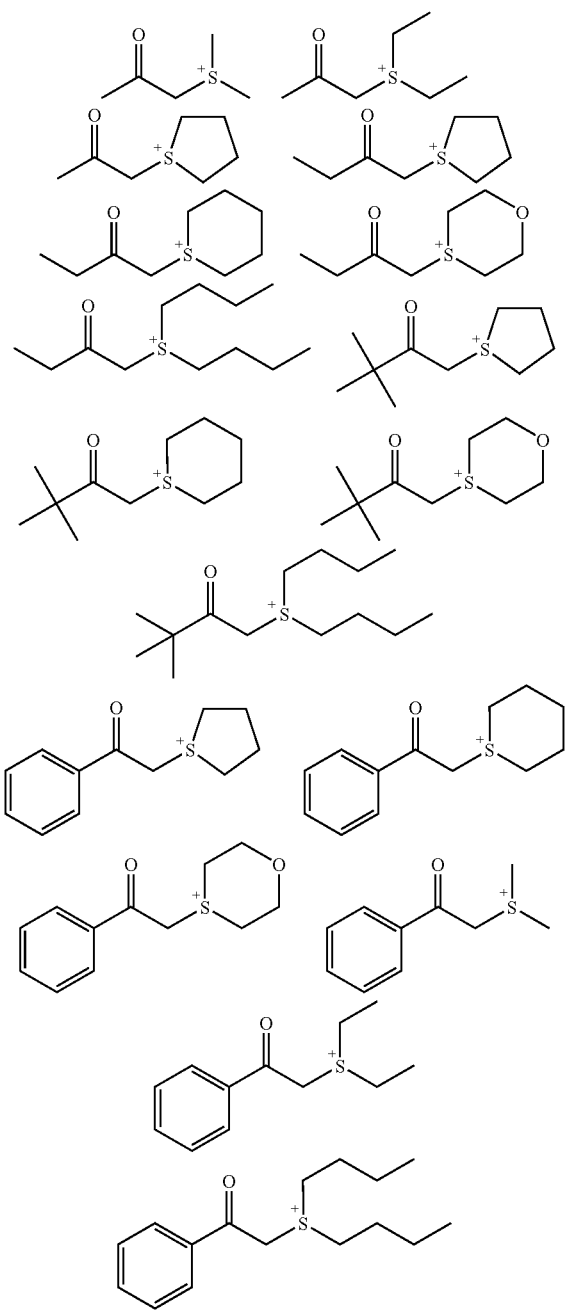
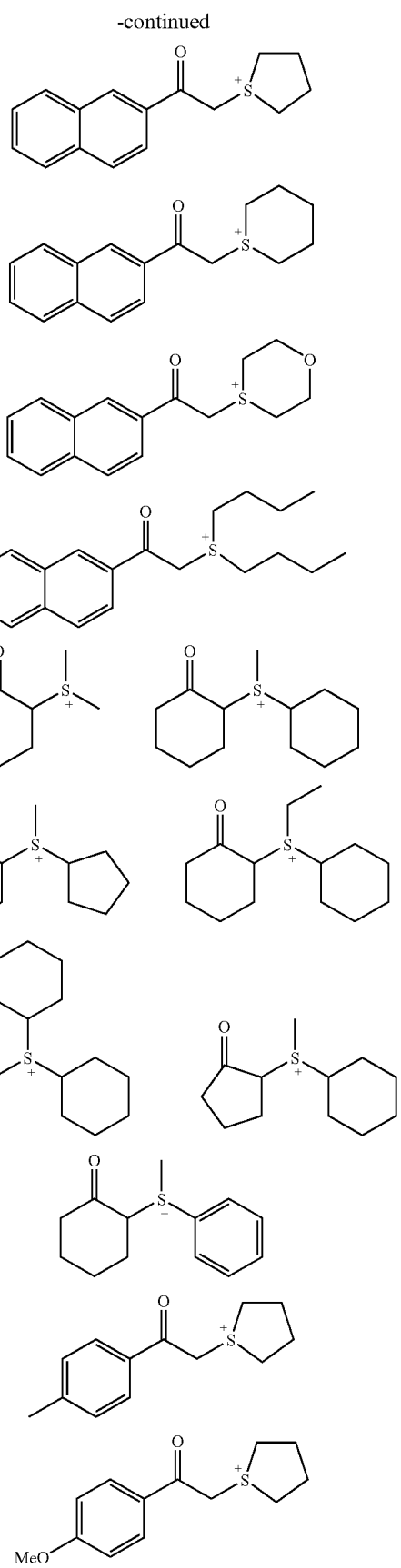

-continued
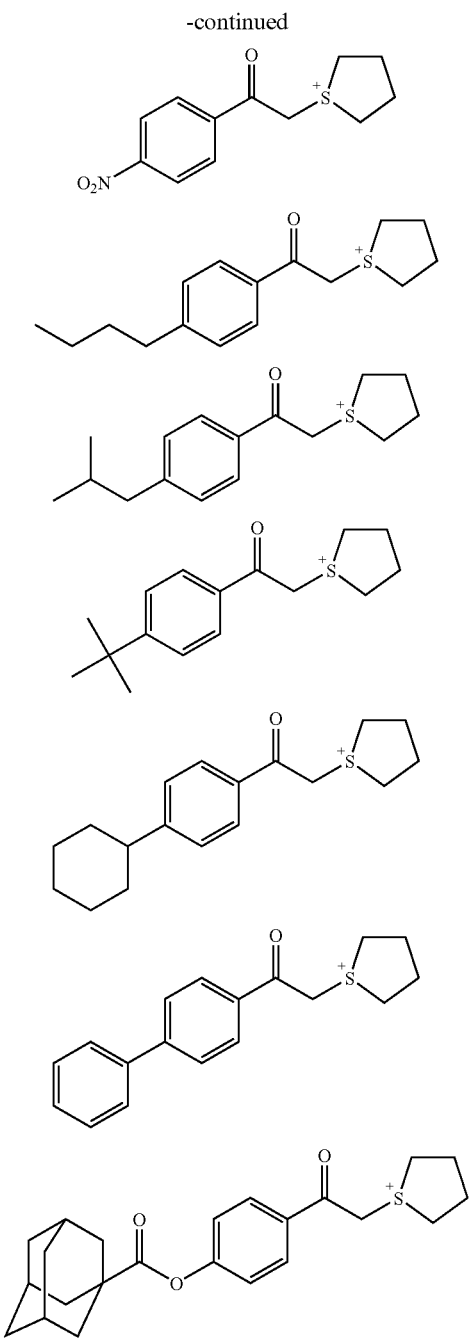
Specific examples of the cation of the formula (IId) include the following:
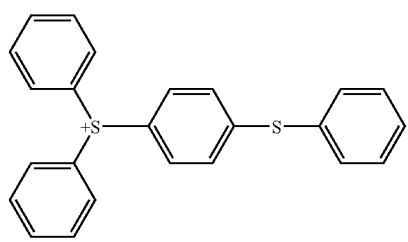
-continued
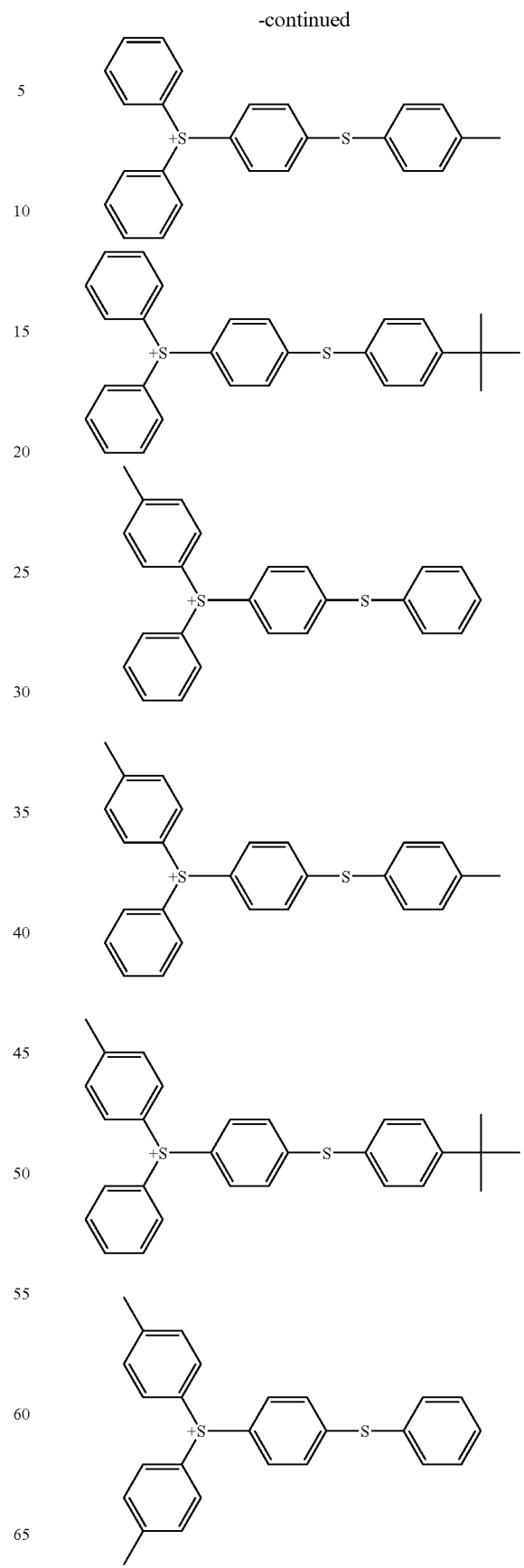

-continued
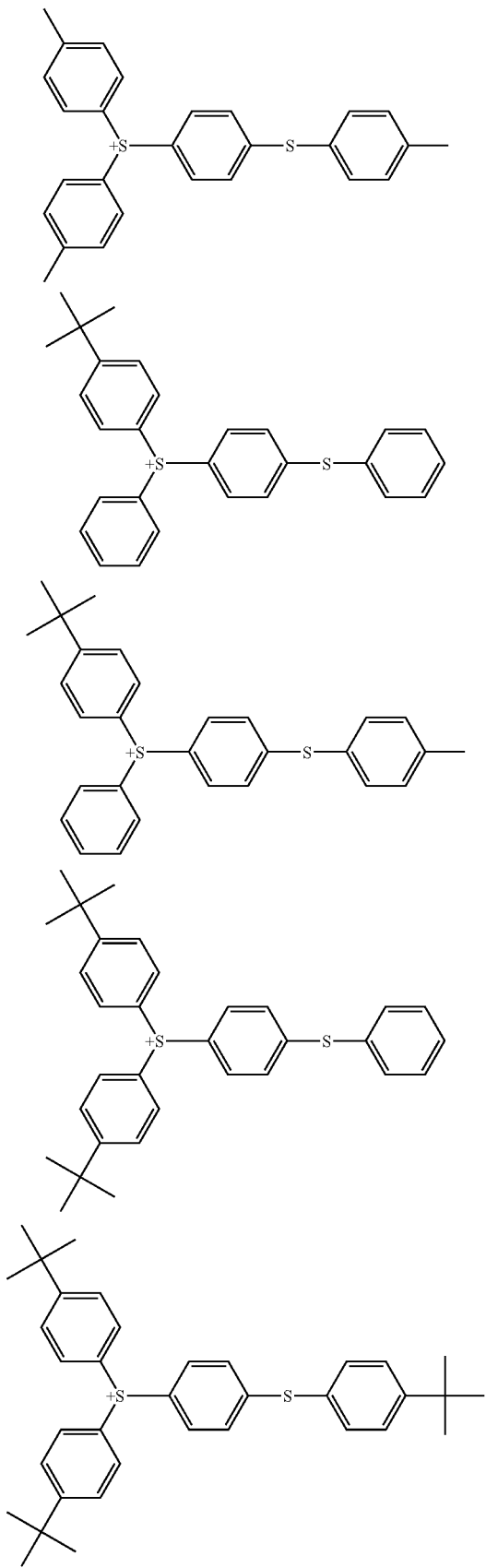
-continued
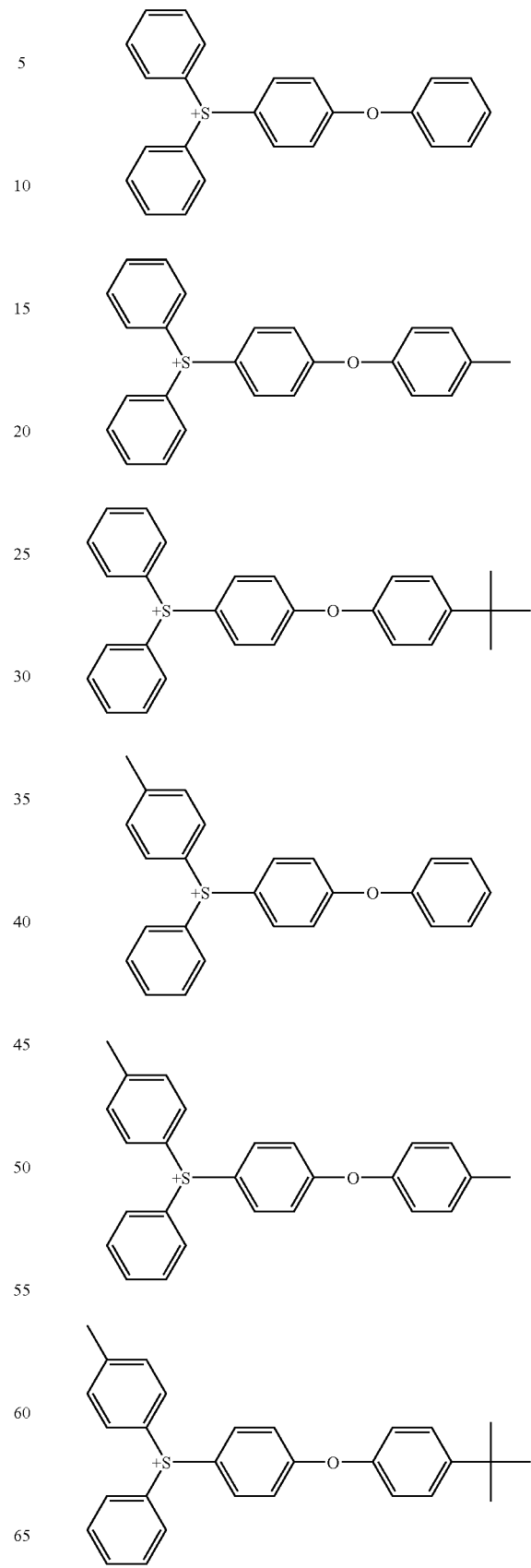

-continued
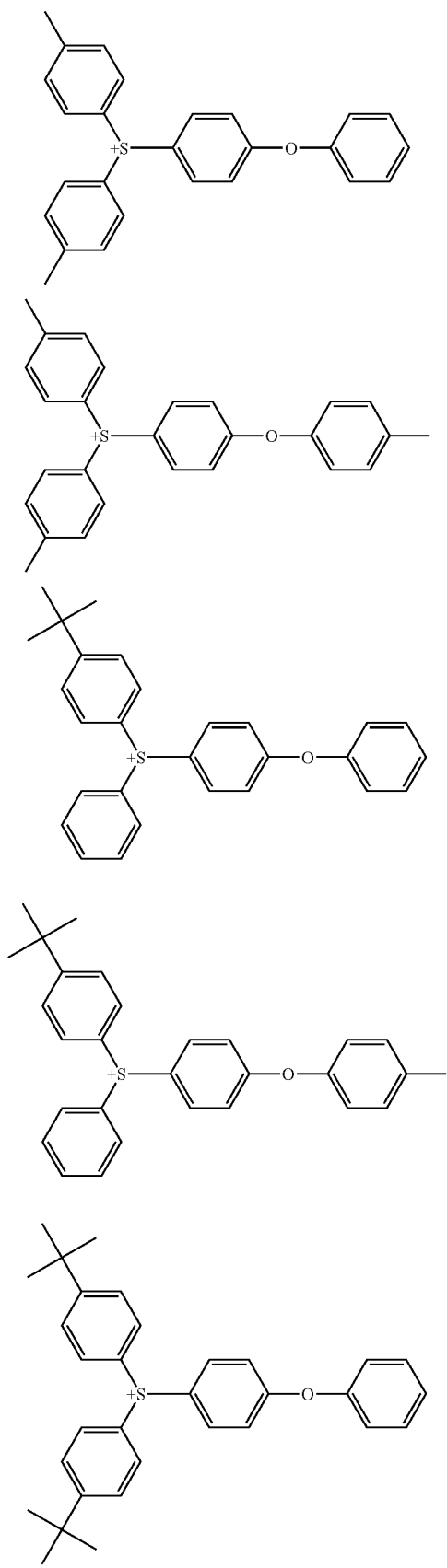
-continued
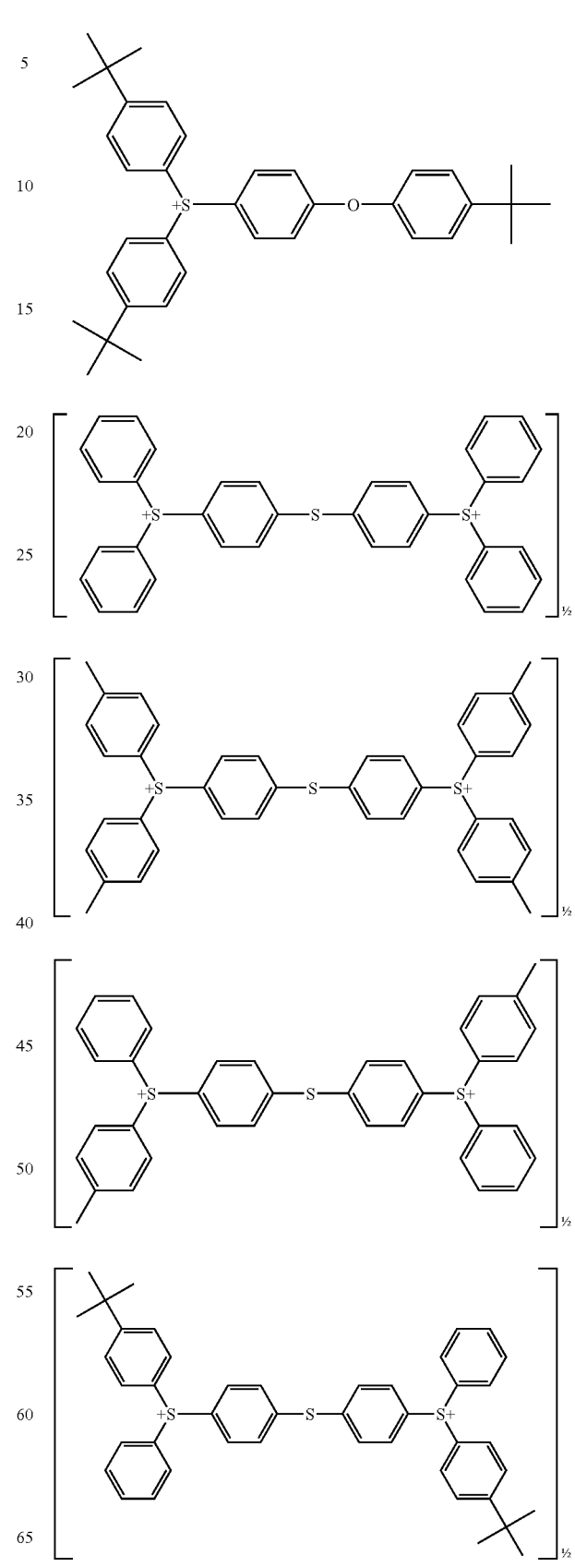

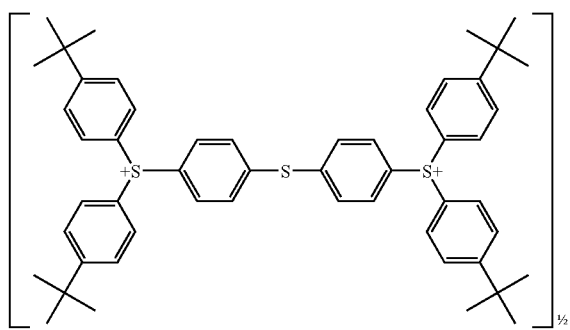
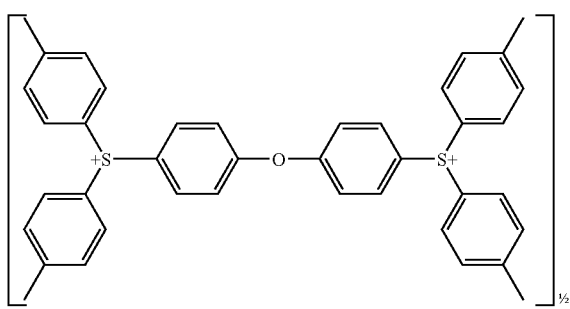
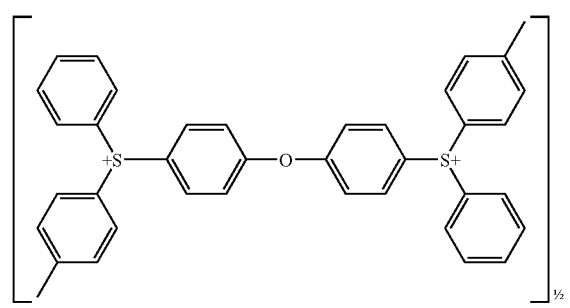
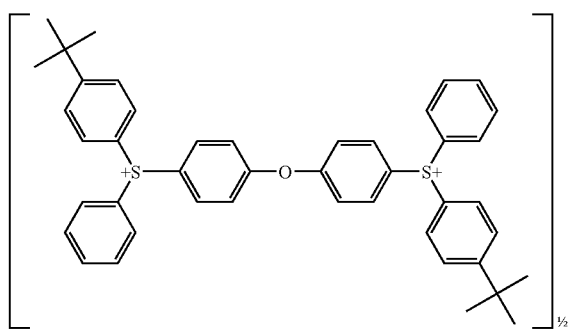
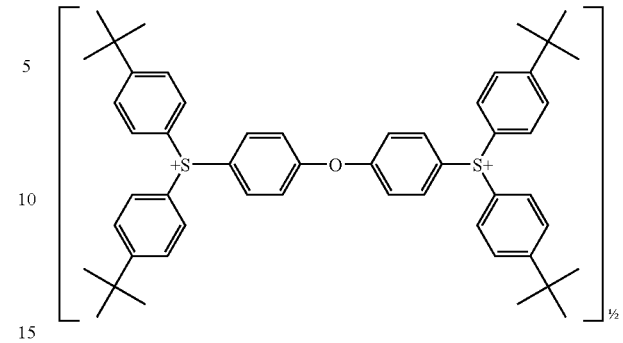
As Salt (I), the salts of the formulae (IIIa), (IIIb) and (IIIc) are preferred for providing chemically amplified resist compositions showing excellent resolution.
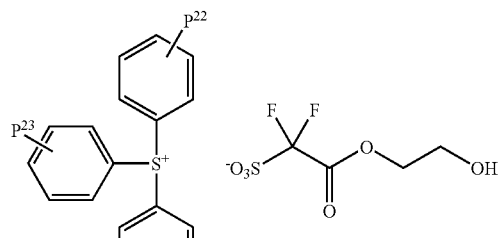
(IIIa)
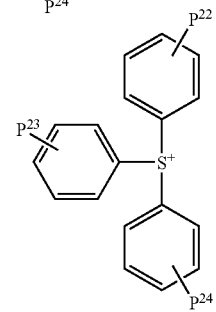
(IIIb)
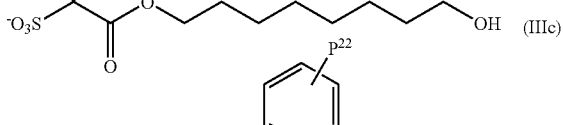
(IIIc)
$P^{22}$, $P^{23}$ and $P^{24}$ have the same meanings as defined above.

Examples of a process for production of Salt (I) include a process comprising reacting an ester of the formula (IV) with an onium salt of the formula (VII), in an inert solvent such as acetonitrile, water, methanol, chloroform and dichloromethane at a temperature of 0 to 150° C., preferably of 0 to 100° C.

The amount of the onium salt of the formula (VII) is usually 0.5 to 2 mol per 1 mol of the ester of the formula (IV). Salt (I) obtained can be taken out by recrystallization when it is in crystal form or by extraction by solvents and concentration when it is in oil form.

Examples of a process for production of the ester of the formula (IV) include a process reacting an alcohol compound of the formula (V) with a carboxylic acid compound of the formula (VI).

The esterification reaction can generally be carried out by mixing materials in an aprotic solvent such as dichloroethane, toluene, ethylbenzene, monochlorobenzene, acetonitrile, N,N-dimethylformamide, and the like, at 20 to 200° C., preferably 50 to 150° C. In the esterification reaction, an acid catalyst or a dehydrating agent is usually added, and examples of the acid catalyst include organic acids such as p-toluenesulfonic acid, inorganic acids such as sulfuric acid, and the like. Examples of the dehydrating agent include 1,1'-carbonyldiimidazole, N,N'-dicyclohexylcarbodiimide, and the like.

The esterification may preferably be carried out with dehydration, for example, by Dean and Stark method as the reaction time tends to be shortened.

The amount of the carboxylic acid compound of the formula (VI) is usually 0.2 to 3 mol, preferably 0.5 to 2 mol per 1 mol of the alcohol compound of the formula (V). The amount of the acid catalyst may be catalytic amount or the amount equivalent to solvent, and is usually 0.001 to 5 mol per 1 mol of the alcohol compound of the formula (V). The amount of the dehydrating agent is usually 0.2 to 5 mol, preferably 0.5 to 3 mol per 1 mol of the alcohol compound of the formula (V).

The present chemically amplified resist composition comprises Salt (I) and a resin which contains a structural unit having an acid-labile group and which itself is insoluble or poorly soluble in an alkali aqueous solution but becomes soluble in an alkali aqueous solution by the action of an acid.

Salt (I) is usually used as an acid generator, and the acid generated by irradiation to Salt (I) catalytically acts against acid-labile groups in a resin, cleaves the acid-labile-group, and the resin becomes soluble in an alkali aqueous solution. Such a composition is suitable for chemically amplified positive resist composition.

The resin used for the present composition contains a structural unit having an acid-labile group and which itself is insoluble or poorly soluble in an alkali aqueous solution, but acid-labile group cleave by an acid. The resin after the cleavage contains carboxylic acid residue and as a result, the resin becomes soluble in an alkali aqueous solution.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, and alicyclic ester group in which a carbon atom adjacent to the oxygen atom is quaternary carbon atom, and the like, a lactone ring group in which a carbon atom adjacent to the oxygen atom is quaternary carbon atom, and the like.

The "quaternary carbon atom" means a "carbon atom joined to four substituents other than hydrogen atom".

Examples of the acid-labile group include alkyl ester group in which a carbon atom adjacent to the oxygen atom is quaternary carbon atom such as tert-butyl ester group; acetal type ester group such as methoxymethyl ester group, ethoxymethyl ester group, 1-ethoxyethyl ester group, 1-isobutoxyethyl ester group, 1-isopropoxyethyl ester group, 1-ethoxypropoxy ester group, 1-(2-methoxyethoxy)ethyl ester, 1-(2-acetoxyethoxy)ethyl ester group, 1-[2-(1-adamantyloxy)ethoxy]ethyl ester group, 1-[2-(1-adamantanecarbonyloxy)ethoxy]ethyl ester group, tetrahydro-2-furyl ester and tetrahydro-2-pyranyl ester group; alicyclic ester group in which a carbon atom adjacent to the oxygen atom is quaternary carbon atom, such as isobornyl ester group, 1-alkylcycloalkyl ester group, 2-alkyl-2-adamantyl ester group, 1-(1-adamantyl)-1-alkylalkyl ester group, and the like.

Examples of structures including the ester group include ester of (meth)acrylic acid structure, ester of norbornenecarboxylic acid structure, ester of tricyclodecenecarboxylic acid structure, tetracyclodecenecarboxylic acid structure, and the like. At least one hydrogen atom in the adamantyl group above may be substituted by hydroxyl group.

The resin used for the present composition can be obtained by addition polymerization of monomer(s) having an acid-labile group and olefinic double bond.

Among the monomers, it is preferable to use those having a bulky group such as alicyclic group (e.g. 2-alkyl-2-adamantyl and 1-(1-adamantyl)-1-alkylalkyl), as the group dissociated by the action of an acid, since excellent resolution is obtained when used in the present composition.

Examples of such monomer containing a bulky group include 2-alkyl-2-adamantyl (meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate, 1-(1-adamantyl)-1-alkylalkyl α-chloroacrylate and the like.

Particularly when 2-alkyl-2-adamantyl (meth)acrylate or 2-alkyl-2-adamantyl α-chloroacrylate is used as the monomer for the resin component in the present composition, resist composition having excellent resolution tend to be obtained. Typical examples of such 2-alkyl-2-adamantyl (meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate and the like. When particularly 2-ethyl-2-adamantyl (meth)acrylate or 2-isopropyl-2-adamantyl (meth)acrylate is used for the present composition, composition having excellent sensitivity and heat resistance tends to be obtained. In the present invention, two or more kind of monomers having group dissociated by the action of an acid may be used together, if necessary.

2-Alkyl-2-adamantyl (meth)acrylate can usually be produced by reacting 2-alkyl-2-adamantanol or metal salt thereof with an acrylic halide or methacrylic halide.

The resin used for the present composition can also contain, in addition to the above-mentioned structural units having an acid-labile group, other structural unit derived from acid-stable monomer. Herein, the "structural unit derived from acid-stable monomer" means "a structural unit not dissociated by an acid generated from Salt (I)".

Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural units derived from 2-norbornene, structural units derived from (meth)acrylonitrile, structural units derived from alkyl (meth)acrylate in which a carbon atom adjacent to oxygen atom is secondary or tertiary carbon atom, structural units derived from 1-adamantyl (meth)acrylate, structural units derived from styrenes such as p- or m-hydroxystyrene, structural units derived from (meth)acryloyloxy-γ-butyrolactone having a lactone ring optionally substituted by alkyl, and the like. Herein, 1-adamantyl ester group is a acid-stable group though the carbon atom adjacent to oxygen atom is a quaternary carbon atom, and at least one hydrogen atom on 1-adamanty ester group may be substituted by hydroxy group.

Specific examples of structural unit derived from acid-stable monomer include a structural unit derived from 3-hydroxyl-1-adamantyl (meth)acrylate, a structural unit derived from 3,5-dihydroxy-1-adamantyl (meth)acrylate, a structural unit derived from α-(meth)acryloyloxy-γ-butyrolactone, a structural unit derived from β-(meth)acryloyloxy-γ-butyrolactone, a structural unit of the following formula (a), a structural unit derived from the following formula (b), a structural unit derived from alicyclic compound having olefinic double bond such as a structural unit of the following formula (c), a structural unit derived from aliphatic unsaturated dicarboxylic anhydride such as a structural unit of the formula (d), a structural unit of the formula (e), and the like.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl (meth)acrylate, a structural unit derived from 3,5-dihydroxy-1-adamantyl (meth)acrylate, a structural unit of the following formula (a) and a structural unit of the following formula (b), in the resin in the present composition, is preferable from the standpoint of the adhesiveness of resist to a substrate and resolution of resist.

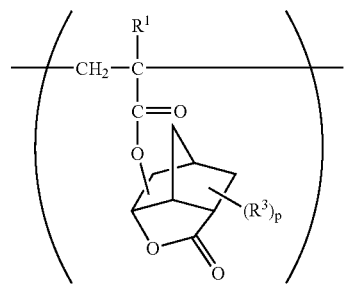

(a)

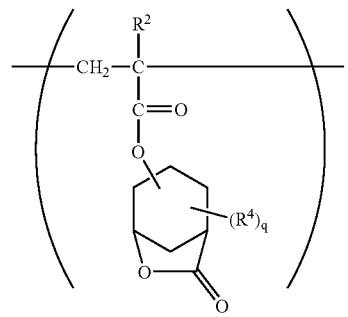

(b)

In the formulae (a) and (b), $R^1$ and $R^2$ each independently represent hydrogen atom, methyl group or trifluoromethyl group and $R^3$ and $R^4$ each independently represent methyl group, trifluoromethyl group or halogen atom, and p and q each independently represent an integer of 0 to 3. When p represents 2 or 3, each of the $R^3$ may be the same or different and when q represents 2 or 3, each of the $R^4$ may be the same or different.

3-Hydroxy-1-adamantyl (meth)acrylate and 3,5-dihydroxy-1-adamantyl (meth)acrylate can be produced, for example, by reacting corresponding hydroxyadamantane with (meth)acrylic acid or its acid halide, and they are also commercially available.

Further, (meth)acryloyloxy-γ-butyrolactone having a lactone ring optionally substituted by alkyl can be produced by reacting corresponding α- or β-bromo-γ-butyrolactone with acrylic acid or methacrylic acid, or reacting corresponding α- or β-hydroxy-γ-butyrolactone with acrylic halide or methacrylic halide.

As monomers to give structural units of the formulae (a) and (b), specifically listed are, for example, (meth)acrylates of alicyclic lactones having hydroxyl described below, and mixtures thereof, and the like. These esters can be produced, for example, by reacting corresponding alicyclic lactone having hydroxyl with (meth)acrylic acids, and the production method thereof is described in, for example, JP2000-26446-A.

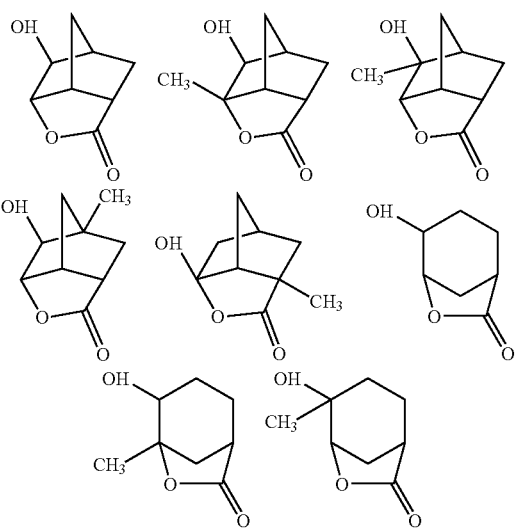

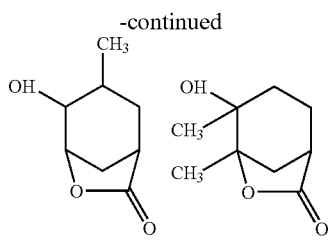

Examples of the (meth)acryloyloxy-γ-butyrolactone having a lactone ring optionally substituted by alkyl include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF lithography, even in the case of using a structure unit derived from hydroxystyrene such as p- and m-hydroxystyrene, as one of the resin components, resist composition having sufficient transparency can be obtained. For obtaining such copolymerization resins, the corresponding (meth)acrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because alicyclic group is directly present on its main chain and shows a property that dry etching resistance is excellent. The structural unit derived from 2-norbornene can be introduced into the main chain by radical polymerization using, for example, in addition to corresponding 2-norbornene, aliphatic unsaturated dicarboxylic anhydrides such as maleic anhydride and itaconic anhydride together. The structural unit derived from 2-norbornene is formed by opening of its double bond, and can be represented by the formula (c). The structural unit derived from maleic anhydride and the structural unit derived from itaconic anhydride which are the structural unit derived from aliphatic unsaturated dicarboxylic anhydrides are formed by opening of their double bonds, and can be represented by the formula (d) and the formula (e), respectively.

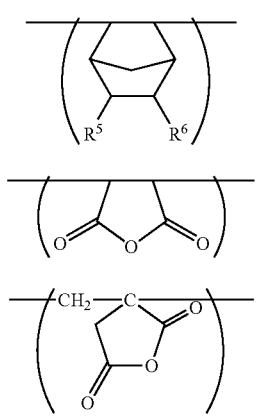

Here, $R^5$ and $R^6$ in the formula (c) each independently represent hydrogen, alkyl having 1 to 3 carbon atoms, hydroxyalkyl having 1 to 3 carbon atoms, carboxyl, cyano or —COOU group in which U represents alcohol residue, or $R^5$ and $R^6$ can bond together to form a carboxylic anhydride residue represented by —C(=O)OC(=O)—.

In $R^5$ and $R^6$, examples of the alkyl include methyl, ethyl, propyl and isopropyl, specific examples of hydroxyalkyl include hydroxymethyl, 2-hydroxyethyl and the like.

In $R^5$ and $R^6$, —COOU group is an ester formed from carboxyl, and as the alcohol residue corresponding to U, for example, optionally substituted alkyls having about 1 to 8 carbon atoms, 2-oxooxolan-3- or -4-yl and the like are listed, and as the substituent on the alkyl, hydroxyl, alicyclic hydrocarbon residues and the like are listed.

Specific examples of the monomer used to give the structural unit represented by the formula (c) may include the followings;
2-norbornene,
2-hydroxy-5-norbornene,
5-norbornen-2-carboxylic acid,
methyl 5-norbornen-2-carboxylate,
2-hydroxyethyl 5-norbornen-2-carboxylate,
5-norbornen-2-methanol,
5-norbornen-2,3-dicarboxylic acid anhydride, and the like.

When U in —COOU is acid-labile group, the structural unit of the formula (c) is a structural unit having acid-labile group even if it has norbornene structure. Examples of monomers giving structural unit having acid-labile group include t-butyl 5-norbornen-2-carboxylate, 1-cyclohexyl-1-methylethyl 5-norbornen-2-carboxylate, 1-methylcyclohexyl 5-norbornen-2-carboxylate, 2-methyl-2-adamantyl 5-norbornen-2-carboxylate, 2-ethyl-2-adamantyl 5-norbornen-2-carboxylate, 1-(4-methylcyclohexyl)-1-methylethyl 5-norbornen-2-carboxylate, 1-(4-hydroxylcydohexyl)-1-methylethyl 5-norbornen-2-carboxylate, 1-methyl-1-(4-oxocyclohexyl)ethyl 5-norbornen-2-carboxylate, 1-(1-adamantyl)-1-methylethyl 5-norbornen-2-carboxylate, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl (meth)acrylate or 1-(1-adamantyl)-1-alkylalkyl (meth)acrylate are used as the acid-labile group, it is advantageous in dry-etching resistance of the resist that the ratio of the structural units is 15% by mol or more in all structural units of the resin.

When, in addition to structural units having an acid-labile group, other structural units having acid-stable group are contained, it is preferable that the sum of these structural units is in the range of 20 to 90% by mol based on all structural units of the resin.

When alicyclic compound having olefinic double bond and aliphatic unsaturated dicarboxylic anhydride are used as copolymerization monomer, it is preferable to use them in excess amount in view of a tendency that these are not easily polymerized.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulae:

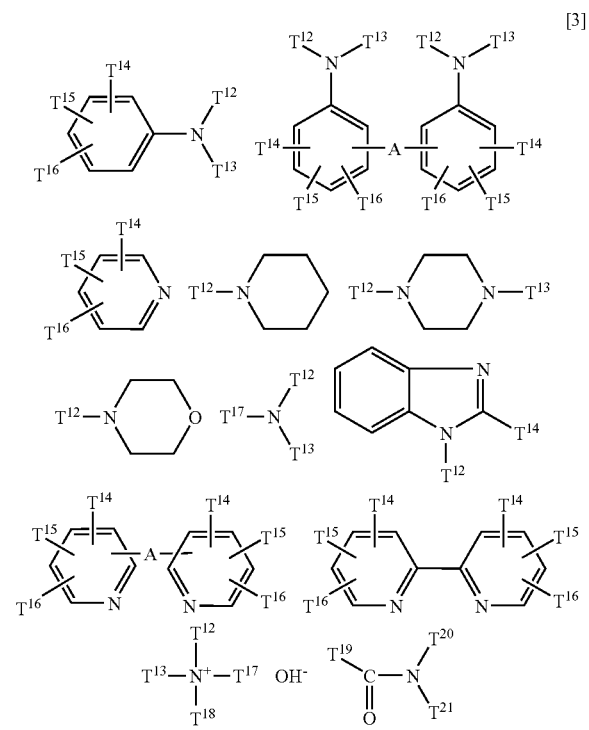

In the formulas, $T^{12}$ and $T^{13}$ each independently represent a hydrogen atom, an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with hydroxyl group, amino group, or alkoxy group having 1 to 6 carbon atoms. At least one hydrogen atom on the amino group may each independently be substituted with alkyl group having 1 to 4 carbon atoms.

$T^{14}$, $T^{15}$ and $T^{16}$ each independently represent a hydrogen atom, an alkyl group, a cycloalkyl group, an aryl group or an alkoxy group. The alkyl group preferably has about 1 to 6 carbon atoms, the cycloalkyl group preferably has about 5 to 10 carbon atoms, the aryl group preferably has about 6 to 10 carbon atoms, and the alkoxy group preferably has about 1 to 6 carbon atoms. Furthermore, at least one hydrogen atom on the alkyl group, cycloalkyl group, aryl group or alkoxy group may each independently be substituted with hydroxyl group, amino group, or alkoxy group having 1 to 6 carbon atoms. At least one hydrogen atom on the amino group may be substituted with alkyl group having 1 to 4 carbon atoms.

$T^{17}$ represents an alkyl group or a cycloalkyl group. The alkyl group preferably has about 1 to 6 carbon atoms, and the cycloalkyl group preferably has about 5 to 10 carbon atoms. Furthermore, at least one hydrogen atom on the alkyl group or cycloalkyl group may each independently be substituted with hydroxyl group, amino group, or alkoxy group having 1 to 6 carbon atoms. At least one hydrogen atom on the amino group may be substituted with alkyl group having 1 to 4 carbon atoms.

In the formulas, $T^{18}$ represents an alkyl group, a cycloalkyl group or an aryl group. The alkyl group preferably has about 1 to 6 carbon atoms, the cycloalkyl group preferably has about 5 to 10 carbon atoms, and the aryl group preferably has about 6 to 10 carbon atoms. Furthermore, at least one hydrogen atom on the alkyl group, cycloalkyl group or aryl group may each independently be substituted with a hydroxyl group, an amino group, or an alkoxy group having 1 to 6 carbon atoms. At least one hydrogen atom on the amino group may each independently be substituted with alkyl group having 1 to 4 carbon atoms.

However, none of $T^{12}$ and $T^{13}$ in the compound represented by the above formula [3] is a hydrogen atom.

A represents alkylene group, carbonyl group, imino group, sulfide group or disulfide group. The alkylene group preferably has about 2 to 6 carbon atoms.

Moreover, among $T^{12}$-$T^{18}$, in regard to those which can be straight-chained or branched, either of these may be permitted.

$T^{19}$, $T^{20}$ and $T^{21}$ each independently represent a hydrogen atom, an alkyl group having 1 to 6 carbon atoms, an aminoalkyl group having 1 to 6 carbon atoms, a hydroxyalkyl group having 1 to 6 carbon atoms or a substituted or unsubstituted aryl group having 6 to 20 carbon atoms, or $T^{19}$ and $T^{20}$ bond to form an alkylene group which forms a lactam ring together with adjacent —CO—N—.

Examples of such compounds include hexylamine, heptylamine, octylamine, nonylamine, decylamine, aniline, 2-, 3- or 4-methylaniline, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylaamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, pyridine, 4-methylpyridine, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "choline"), N-methylpyrrolidone, and the like.

Furthermore, hindered amine compounds having piperidine skeleton as disclosed in JP-A-H11-52575 can be used as quencher.

It is preferable that the present composition contains resin component in an amount of about 80 to 99.9% by weight and Salt (I) in an amount of 0.1 to 20% by weight on the total amount of the resin component and Salt (I).

When basic compound is used as a quencher, the basic compound is contained preferably in an amount of about 0.01 to 1 part by weight per 100 parts by weight of sum of resin component and Salt (I).

The present composition can contain, if necessary, various additives in small amount such as a sensitizer, solution suppressing agent, other polymers, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethyl Cellosolve acetate, methyl Cellosolve acetate and propylene glycol monomethyl ether acetate; glycol ethers such as propylene glycol monomethyl ether, di(ethylene glycol) dimethyl ether; esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by way of examples, which are not construed to limit the scope of the present invention. The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns): TSKgel Multipore HXL-M, Solvent: Tetrahydrofuran, manufactured by TOSOH CORPORATION] using styrene as a standard reference material. Structures of compounds were determined by NMR (GX-270 Type, or EX-270 Type, manufactured by JEOL LTD) and mass spectrometry (Liquid Chromatography: 1100 Type, manufactured by Hewlett Packard, Mass Spectrometry: LC/MSD Type, manufactured by Hewlett Packard).

EXAMPLE 1

Synthesis of triphenylsulfonium (2-hydroxyethoxycarbonyl)difluoromethanesulfonate (1) 230 Parts of 30% aqueous sodium hydroxide solution was added into a mixture of 100 parts of methyl difluoro (fluorosulfonyl)acetate and 250 parts of ion-exchanged water in a ice bath. The added mixture was heated and refluxed at 100° C. for 3 hours. After cooling, the cooled mixture was neutralized with 88 parts of conc. hydrochloric acid and concentrated to obtain 165.0 parts of sodium difluorosulfoacetate (containing inorganic salt, purity: 62.5%).

(2) 8.0 Parts of sodium difluorosulfoacetate (purity: 62.5%), 1.57 parts of ethylene glycol and 60 parts of dichloroethane were charged in a vessel, 1.24 parts of sulfuric acid was added thereto, and the mixture was refluxed for 4 hours. After concentrating the mixture to eliminate dichloroethane, 100 parts of ethyl acetate was added thereto, and the added mixture was stirred. The stirred mixture was filtrated and concentrated to obtain 9.25 parts of sodium salt of 2-hydroxyethyl difluorosulfoacetate.

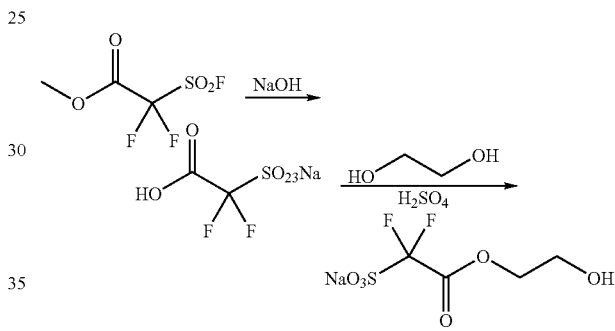

$^1$H-NMR data of sodium salt of 2-hydroxyethyl difluorosulfoacetate (dimethylsulfoxide-$d_6$, Internal Standard: tetramethylsilane): d(ppm) 3.60(q, 2H); 4.22(t, 2H); 4.82(br, 1H)

(3) 9.25 Parts of sodium salt of 2-hydroxyethyl difluorosulfoacetate obtained in (2) was dissolved in 92.5 parts of acetonitrile. 11.4 parts of triphenylsulfonium chloride and 57 parts of ion-exchanged water were added to the solution. After stirred for 15 hours, the stirred mixture was concentrated and extracted first with 100 parts of and then with 50 parts of chloroform. The organic layers were mixed and washed with ion-exchanged water. The obtained organic layer was concentrated. The concentrate was washed with each of 50 parts of tert-butyl methyl ether and 50 parts of ethyl acetate and each of the solvent was decanted to obtain 5.54 parts of triphenylsulfonium (2-hydroxyethoxycarbonyl)difluoromethanesulfonate in the form of white solid, which is called as acid generator B1.

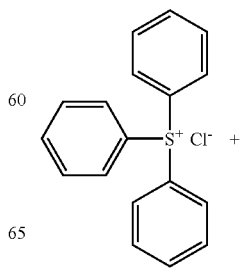

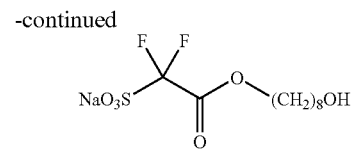

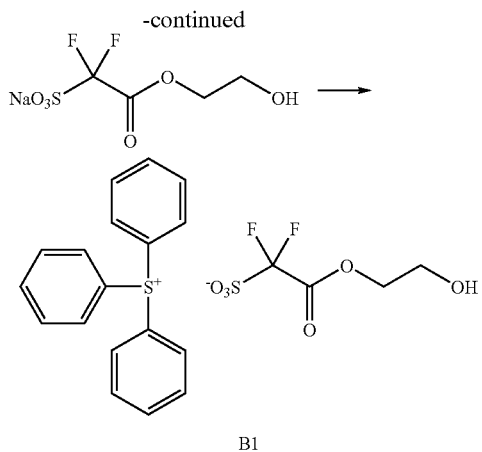

B1

$^1$H-NMR data of acid generator B1 (dimethylsulfoxide-d$_6$, Internal Standard: tetramethylsilane): d(ppm)
3.58(q, 2H); 4.20(t, 2H); 4.78(t, 1H); 7.74-7.89(m, 15H)
MS(ESI(+) Spectrum): M+263.2 (C$_{18}$H$_{15}$S$^+$=263.09)
MS(ESI(−) Spectrum): M−219.0 (C$_4$H$_5$F$_2$O$_6$S$^-$=218.98)

EXAMPLE 2

Synthesis of triphenylsulfonium (8-hydroxyoctyloxycarbonyl)difluoromethanesulfonate (1) 424 Parts of 30% aqueous sodium hydroxide solution was added into a mixture of 500 parts of methyl difluoro (fluorosulfonyl)acetate and 750 parts of ion-exchanged water in a ice bath. The added mixture was heated and refluxed at 100° C. for 2.5 hours. After cooling, the cooled mixture was neutralized with 440 parts of conc. hydrochloric acid and concentrated to obtain 802.82 parts of sodium difluorosulfoacetate (containing inorganic salt, purity: 64.2%).

(2) 5.0 Parts of sodium difluorosulfoacetate (purity: 64.2%), 2.32 parts of 1,8-octane diol and 60 parts of dichloroethane were charged in a vessel, 3.02 parts of p-toluenesulfonic acid (p-TsOH) was added thereto, and the mixture was refluxed for 4.5 hours. After concentrating the mixture to eliminate dichloroethane, 100 parts of t-butyl methyl ether was added thereto and washed, and then the solvent was decanted. The washed mixture was concentrated. 100 parts of acetonitrile was added thereto, and the added mixture was stirred. The stirred mixture was filtrated and concentrated to obtain 2.82 parts of sodium salt of 8-hydroxyoctyl difluorosulfoacetate. (containing diester compound, purity:41.2%)

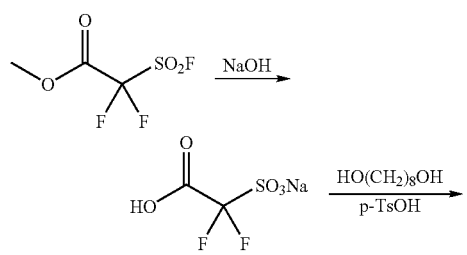

$^1$H-NMR data of sodium salt of 8-hydroxyoctyl difluorosulfoacetate (dimethylsulfoxide-d$_6$, Internal Standard: tetramethylsilane): d(ppm) 1.26-1.43(m, 10H); 1.56-1.65(m, 2H); 3.37(t, 2H); 4.19(t, 2H)

(3) 2.82 Parts of sodium salt of 8-hydroxyoctyl difluorosulfoacetate obtained in (2) was dissolved in 28.2 parts of acetonitrile. 3.19 parts of triphenylsulfonium chloride and 31.9 parts of ion-exchanged water were added to the solution. After stirred for 15 hours, the stirred mixture was concentrated and extracted with 50 parts of chloroform twice. The organic layers were mixed and washed with ion-exchanged water. The obtained organic layer was concentrated. The concentrate was washed with of 30 parts of tert-butyl methyl ether and the solvent was decanted. Then the washed concentrate was extracted first with 50 parts of and then 200 parts of ethyl acetate. The organic layers were mixed and concentrated to obtain 0.73 part of triphenylsulfonium (8-hydroxyoctyloxycarbonyl)difluoromethanesulfonate in the form of colorless liquid, which is called as acid generator B2.

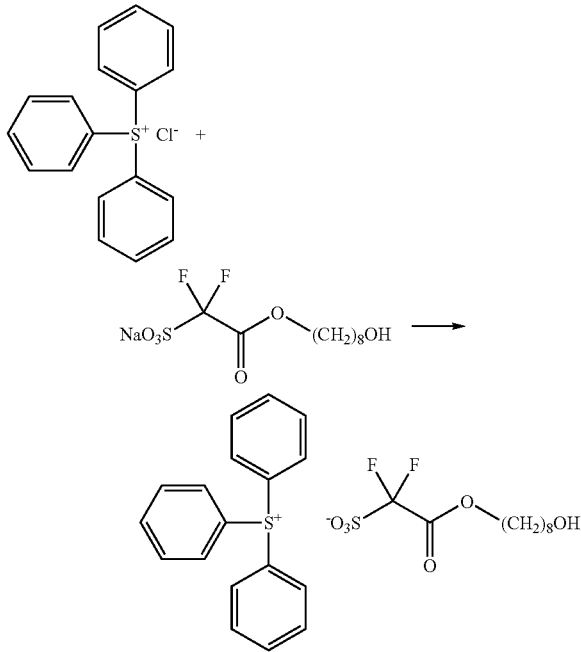

B2

$^1$H-NMR data of acid generator B2 (dimethylsulfoxide-d$_6$, Internal Standard: tetramethylsilane): d(ppm)
1.26-1.42(m, 10H); 1.54-1.64(m, 2H); 3.38(t, 2H); 4.18(t, 2H); 4.31(t, 1H); 7.75-7.90(m, 15H)
MS(ESI(+) Spectrum): M+263.2 (C$_{18}$H$_{15}$S$^+$=263.09)
MS(ESI(−) Spectrum): M−303.2 (C$_{10}$H$_{17}$F$_2$O$_6$S$^-$=303.07)

EXAMPLE 3

Synthesis of triphenylsulfonium ((4-hydroxymethyl-cyclohexyl)methoxycarbonyl)-difluoromethane-sulfonate (1) 230 Parts of 30% aqueous sodium hydroxide solution was added into a mixture of 100 parts of methyl difluoro (fluorosulfonyl)acetate and 250 parts of ion-exchanged water in a ice bath. The added mixture was heated and refluxed at 100° C. for 3 hours. After cooling, the cooled mixture was neutralized with 88 parts of conc. hydrochloric acid and concentrated to obtain 165.0 parts of sodium difluorosulfoacetate (containing inorganic salt, purity: 62.5%).

(2) 5.0 Parts of sodium difluorosulfoacetate (purity: 62.5%), 2.28 parts of 1,4-cyclohexane dimethanol and 60 parts of dichloroethane were charged in a vessel, 3.00 parts of p-toluenesulfonic acid (p-TsOH) was added thereto, and the mixture was refluxed for 0.6 hour. After concentrating the mixture to eliminate dichloroethane, 100 parts of acetonitrile was added thereto and the mixture was stirred. The stirred mixture was filtrated and concentrated to obtain 6.78 parts of sodium salt of 4-hydroxymethylcyclohexylmethyl difluorosulfoacetate. (containing 1,4-cyclohexane dimethanol and diester)

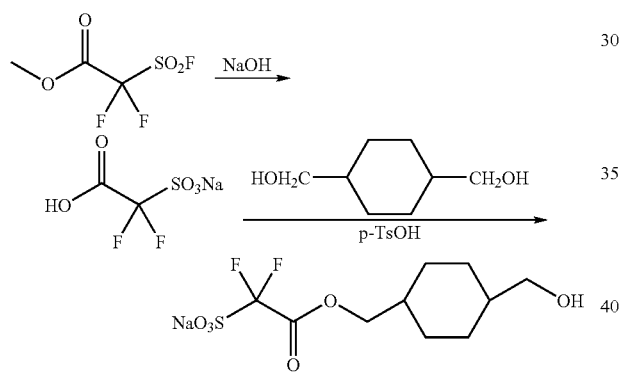

$^1$H-NMR data of sodium salt of 4-hydroxymethylcyclohexylmethyl difluorosulfoacetate (dimethylsulfoxide-$d_6$, Internal Standard: tetramethylsilane): d(ppm) 0.76-1.01(m, 4H); 1.27(br, 1H); 1.57(br, 1H); 1.73(d, 4H); 3.20(t, 2H); 4.03(d, 2H); 4.70(br, 1H)

(3) 6.78 Parts of sodium salt of 4-hydroxymethylcyclohexylmethyl difluorosulfoacetate obtained in (2) was dissolved in 67.8 parts of acetonitrile. 6.25 parts of triphenylsulfonium chloride and 62.5 parts of ion-exchanged water were added to the solution. After stirred for 15 hours, the stirred mixture was concentrated and 250 parts of chloroform was added thereto. The added mixture was filtrated to eliminate undissolved substance. The organic layer was washed with ion-exchanged water. The obtained organic layer was concentrated. The concentrate was washed with 30 parts of tert-butyl methyl ether and the solvent was decanted. Then 10 parts of acetonitrile was added thereto and the mixture was filtrated to eliminate undissolved substance. The addition and filtration were repeated two more times. The filtrated solution was concentrated to obtain 1.81 parts of triphenylsulfonium ((4-hydroxymethylcyclohexyl)methoxycarbonyl)difluoromethanesulfonate in the form of colorless liquid, which is called as acid generator B3.

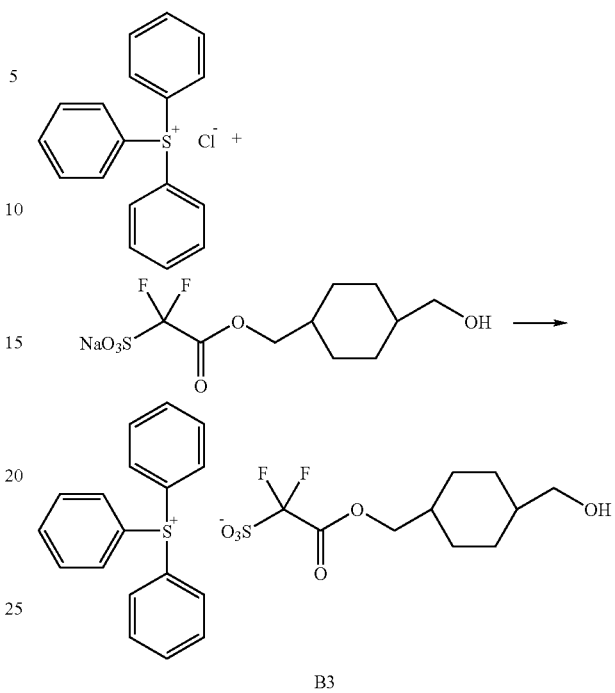

B3

$^1$H-NMR data of acid generator B3 (dimethylsulfoxide-$d_6$, Internal Standard: tetramethylsilane): d(ppm) 0.77-1.03 (m, 4H); 1.28(br, 1H); 1.57(br, 1H); 1.73(d, 4H); 3.19(t, 2H); 4.02(d, 2H); 4.35(t, 1H); 7.75-7.90(m, 15H)

MS(ESI(+) Spectrum): M+263.2 ($C_{18}H_{15}S^+$=263.09)

MS(ESI(-) Spectrum): M−301.0($C_{10}H_{15}F_2O_6S^-$=301.06)

EXAMPLE 4

Synthesis of triphenylsulfonium (2-(2-(2-hydroxyethoxy)ethoxy)ethoxycarbonyl)-difluoromethane-sulfonate (1) 424 Parts of 30% aqueous sodium hydroxide solution was added into a mixture of 500 parts of methyl difluoro (fluorosulfonyl)acetate and 750 parts of ion-exchanged water in a ice bath. The added mixture was heated and refluxed at 100° C. for 2.5 hours. After cooling, the cooled mixture was neutralized with 440 parts of conc. hydrochloric acid and concentrated to obtain 802.82 parts of sodium difluorosulfoacetate (containing inorganic salt, purity: 64.2%).

(2) 5.0 Parts of sodium difluorosulfoacetate (purity: 64.2%), 2.43 parts of triethylene glycol and 60 parts of dichloroethane were charged in a vessel, 3.08 parts of p-toluenesulfonic acid (p-TsOH) was added thereto, and the mixture was refluxed for 12 hours. After concentrating the mixture to eliminate dichloroethane, 100 parts of t-butyl methyl ether was added thereto and washed. Then the solvent was decanted and the residue was filtrated. 100 Parts of acetonitrile was added thereto, and the added mixture was stirred. The stirred mixture was filtrated and concentrated to obtain 5.06 parts of sodium salt of 2-(2-(2-hydroxylethoxy)ethoxy)ethyl difluorosulfoacetate. (containing triethylene glycol and diester compound)

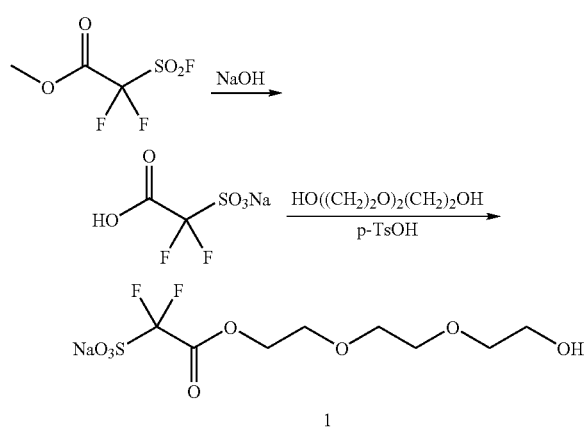

H-NMR data of sodium salt of 2-(2-(2-hydroxylethoxy)ethoxy)ethyl difluorosulfoacetate (dimethylsulfoxide-d₆, Internal Standard: tetramethylsilane): d(ppm) 3.38-3.40(m, 2H); 3.46-3.54(m, 6H); 3.62-3.65(m, 2H); 4.28-4.32(m, 2H); 4.56(br, 1H)

(3) 5.06 Parts of sodium salt of 2-(2-(2-hydroxyethoxy)ethoxy)ethyl difluorosulfoacetate obtained in (2) was dissolved in 50.6 parts of acetonitrile. 6.87 parts of triphenylsulfonium chloride and 34.3 parts of ion-exchanged water were added to the solution. After stirred for 15 hours, the stirred mixture was concentrated and extracted first with 100 parts of and then with 50 parts of chloroform. The organic layers were mixed and washed with ion-exchanged water. The obtained organic layer was concentrated. The concentrate was washed with each of 20 parts of tert-butyl methyl ether and 20 parts of ethyl acetate and each of the solvent was decanted. The washed concentrate was extracted with 200 parts of ethyl acetate twice, with a mixed solvent consisting of 5 parts of acetonitrile and 200 parts of ethyl acetate, and a mixed solvent consisting of 10 parts of acetonitrile and 200 parts of ethyl acetate to obtain 0.91 part of triphenylsulfonium (2-(2-(2-hydroxyethoxy)ethoxy)ethoxycarbonyl)-difluoromethanesulfonate in the form of colorless liquid, which is called as acid generator B4.

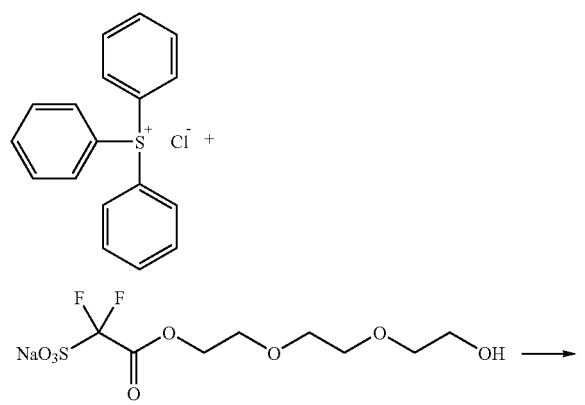

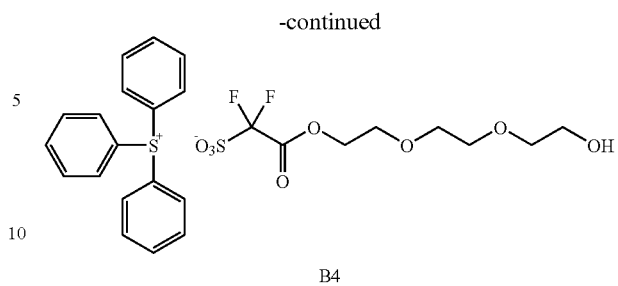

¹H-NMR data of acid generator B4 (dimethylsulfoxide-d₆, Internal Standard: tetramethylsilane): d(ppm) 3.39-3.43 (m, 2H); 3.45-3.58(m, 6H); 3.63-3.66(m, 2H); 4.29-4.33(m, 2H); 4.57(t, 1H); 7.75-7.90(m, 15H)

MS(ESI(+) Spectrum): M+263.0 ($C_{18}H_{15}S^+$=263.09)

MS(ESI(−) Spectrum): M−307.0 ($C_8H_{13}F_2O_8S^-$=307.03)

EXAMPLE 5

Synthesis of triphenylsulfonium (2-methoxyethoxycarbonyl)difluoromethanesulfonate (1) 424 Parts of 30% aqueous sodium hydroxide solution was added into a mixture of 500 parts of methyl difluoro (fluorosulfonyl)acetate and 750 parts of ion-exchanged water in a ice bath. The added mixture was heated and refluxed at 100° C. for 2.5 hours. After cooling, the cooled mixture was neutralized with 440 parts of conc. hydrochloric acid and concentrated to obtain 802.82 parts of sodium difluorosulfoacetate (containing inorganic salt, purity: 64.2%).

(2) 5.0 Parts of sodium difluorosulfoacetate (purity: 64.2%), 1.23 parts of 2-methoxymethanol and 60 parts of dichloroethane were charged in a vessel, 3.08 parts of p-toluenesulfonic acid (p-TsOH) was added thereto, and the mixture was refluxed for 10 hours. After concentrating the mixture to eliminate dichloroethane, 100 parts of t-butyl methyl ether was added thereto and washed. Then the solvent was decanted and the residue was filtrated. 100 Parts of acetonitrile was added thereto, and the added mixture was stirred. The stirred mixture was filtrated and concentrated to obtain 1.01 parts of sodium salt of 2-methoxyethyl difluorosulfoacetate.

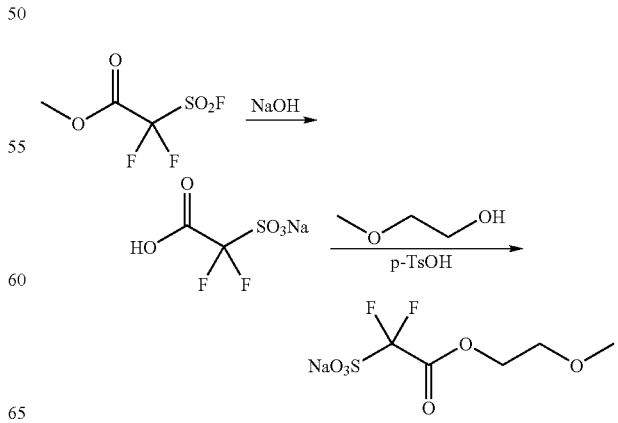

H-NMR data of sodium salt of 2-methoxyethyl difluorosulfoacetate (dimethylsulfoxide-d$_6$, Internal Standard: tetramethylsilane): d(ppm) 3.27(s, 3H); 3.54-3.58(m, 2H); 4.30-4.33(m, 2H)

(3) 1.01 Parts of sodium salt of 2-methoxyethyl difluorosulfoacetate obtained in (2) was dissolved in 10.1 parts of acetonitrile. 1.18 parts of triphenylsulfonium chloride and 5.9 parts of ion-exchanged water were added to the solution. After stirred for 15 hours, the stirred mixture was concentrated. The concentrate was extracted with 50 parts of chloroform twice. The organic layers were mixed and washed with ion-exchanged water. The washed organic layer was concentrated. The concentrate was washed with of 20 parts of tert-butyl methyl ether and the solvent was decanted to obtain 0.84 part of triphenylsulfonium (2-methoxyethoxycarbonyl)difluoromethanesulfonate in the form of white solid, which is called as acid generator B5.

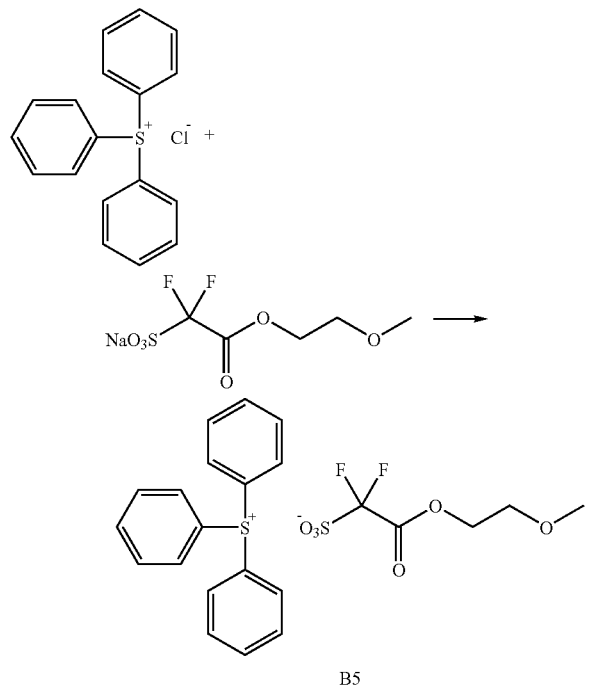

B5

$^1$H-NMR data of acid generator B5 (dimethylsulfoxide-d$_6$, Internal Standard: tetramethylsilane): d(ppm) 3.27(s, 3H); 3.54-3.57(m, 2H); 4.29-4.33(m, 2H);7.75-7.90(m, 15H)

MS(ESI(+) Spectrum): M+263.0 (C$_{18}$H$_{15}$S$^+$=263.09)
MS(ESI(−) Spectrum): M−233.0 (C$_5$H$_7$F$_2$O$_6$S$^-$=232.99)

EXAMPLE 6

Synthesis of triphenylsulfonium (2-(2-methoxyethoxy)ethoxycarbonyl)difluoromethanesulfonate (1) 424 Parts of 30% aqueous sodium hydroxide solution was added into a mixture of 500 parts of methyl difluoro(fluorosulfonyl)acetate and 750 parts of ion-exchanged water in a ice bath. The added mixture was heated and refluxed at 100° C. for 2.5 hours. After cooling, the cooled mixture was neutralized with 440 parts of conc. hydrochloric acid and concentrated to obtain 802.82 parts of sodium difluorosulfoacetate (containing inorganic salt, purity: 64.2%).

(2) 5.0 Parts of sodium difluorosulfoacetate (purity: 64.2%), 1.95 parts of 2-(2-methoxyethoxy)ethanol and 60 parts of dichloroethane were charged in a vessel, 3.08 parts of p-toluenesulfonic acid (p-TsOH) was added thereto, and the mixture was refluxed for 12 hours. After concentrating the mixture to eliminate dichloroethane, 100 parts of t-butyl methyl ether was added thereto and washed. Then the solvent was decanted and the residue was filtrated. 100 Parts of acetonitrile was added thereto, and the added mixture was stirred. The stirred mixture was filtrated and concentrated to obtain 2.82 parts of sodium salt of 2-(2-methoxyethoxy)ethyl difluorosulfoacetate.

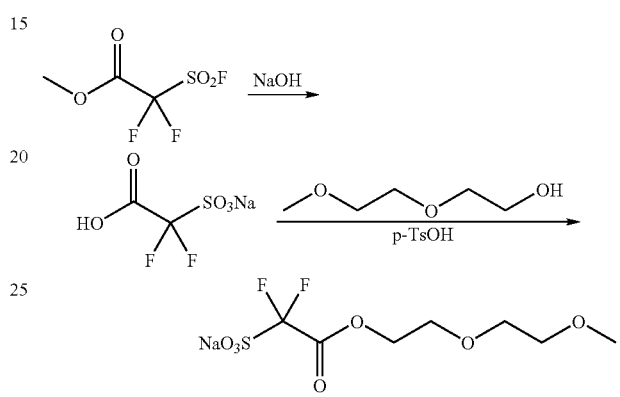

H-NMR data of sodium salt of 2-(2-methoxyethoxy)ethyl difluorosulfoacetate (dimethylsulfoxide-d$_6$, Internal Standard: tetramethylsilane): d(ppm) 3.24(s, 3H); 3.41-3.45(m, 2H); 3.54-3.57(m, 2H); 3.62-3.66(m,2H); 4.29-4.33(m, 2H)

(3) 2.82 Parts of sodium salt of 2-(2-methoxyethoxy)ethyl difluorosulfoacetate obtained in (2) was dissolved in 28.2 parts of acetonitrile. 2.81 parts of triphenylsulfonium chloride and 14.0 parts of ion-exchanged water were added to the solution. After stirred for 15 hours, the stirred mixture was concentrated. The concentrate was extracted first with 100 parts of and then with 50 parts of chloroform. The organic layers were mixed and washed with ion-exchanged water. The washed organic layer was concentrated. The concentrate was washed with of 20 parts of tert-butyl methyl ether and the solvent was decanted to obtain 3.47 part of triphenylsulfonium (2-(2-methoxyethoxy)ethoxycarbonyl)difluoromethanesulfonate in the form of colorless liquid, which is called as acid generator B6.

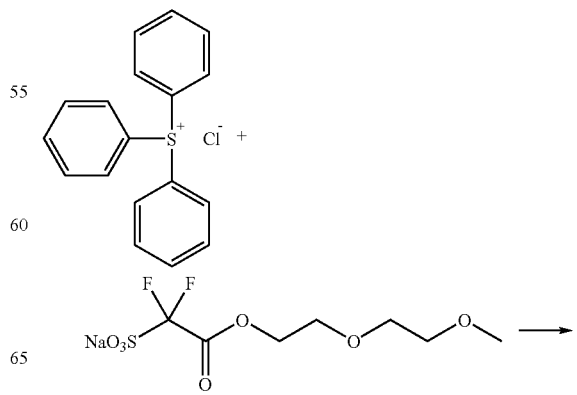

-continued

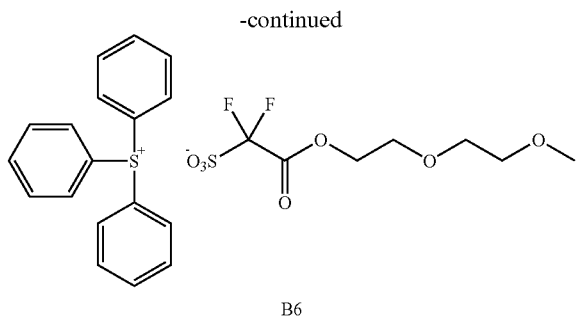

B6

H-NMR data of acid generator B6 (dimethylsulfoxide-$d_6$, Internal Standard: tetramethylsilane): d(ppm) 3.23(s, 3H); 3.41-3.44(m, 2H); 3.53-3.57(m, 2H); 3.62-3.66(m, 2H); 4.29-4.32(m, 2H); 7.76-7.91(m, 15H)

MS(ESI(+) Spectrum): M+263.0 ($C_{18}H_{15}S^+$=263.09)

MS(ESI(−) Spectrum): M−277.0 ($C_7H_{11}F_2O_7S^-$=277.02)

EXAMPLE 7

Synthesis of triphenylsulfonium (2-cyanoethoxycarbonyl)difluoromethanesulfonate (1) 424 Parts of 30% aqueous sodium hydroxide solution was added into a mixture of 500 parts of methyl difluoro (fluorosulfonyl)acetate and 750 parts of ion-exchanged water in a ice bath. The added mixture was heated and refluxed at 100° C. for 2.5 hours. After cooling, the cooled mixture was neutralized with 440 parts of conc. hydrochloric acid and concentrated to obtain 802.82 parts of sodium difluorosulfoacetate (containing inorganic salt, purity: 64.2%).

(2) 5.0 Parts of sodium difluorosulfoacetate (purity: 64.2%), 1.15 parts of 2-cyanoethanol and 60 parts of dichloroethane were charged in a vessel, 3.08 parts of p-toluenesulfonic acid (p-TsOH) was added thereto, and the mixture was refluxed for 10 hours. After concentrating the mixture to eliminate dichloroethane, 100 parts of t-butyl methyl ether was added thereto and washed. Then the solvent was decanted and the residue was filtrated. 100 Parts of acetonitrile was added thereto, and the added mixture was stirred. The stirred mixture was filtrated and concentrated to obtain 2.40 parts of sodium salt of 2-cyanoethyl difluorosulfoacetate.

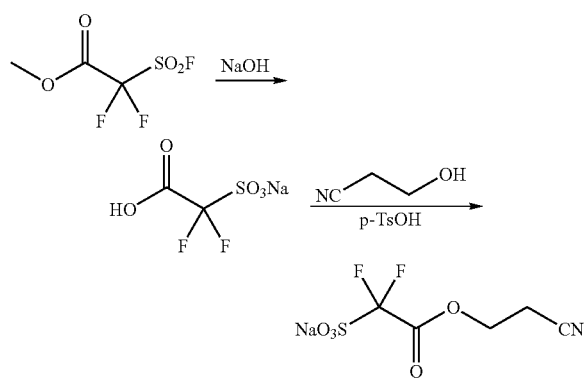

H-NMR data of sodium salt of 2-cyanoethyl difluorosulfoacetate (dimethylsulfoxide-$d_6$, Internal Standard: tetramethylsilane): d(ppm) 2.94(t, 2H); 4.41(t, 2H)

(3) 2.40 Parts of sodium salt of 2-cyanoethyl difluorosulfoacetate obtained in (2) was dissolved in 24.0 parts of acetonitrile. 2.82 parts of triphenylsulfonium chloride and 14.11 parts of ion-exchanged water were added to the solution. After stirred for 15 hours, the stirred mixture was concentrated. The concentrate was extracted with 50 parts of chloroform twice. The organic layers were mixed and washed with ion-exchanged water. The washed organic layer was concentrated. The concentrate was washed with of 20 parts of tert-butyl methyl ether and the solvent was decanted to obtain 0.71 part of triphenylsulfonium (2-cyanoethoxycarbonyl)difluoromethanesulfonate in the form of colorless liquid, which is called as acid generator B7.

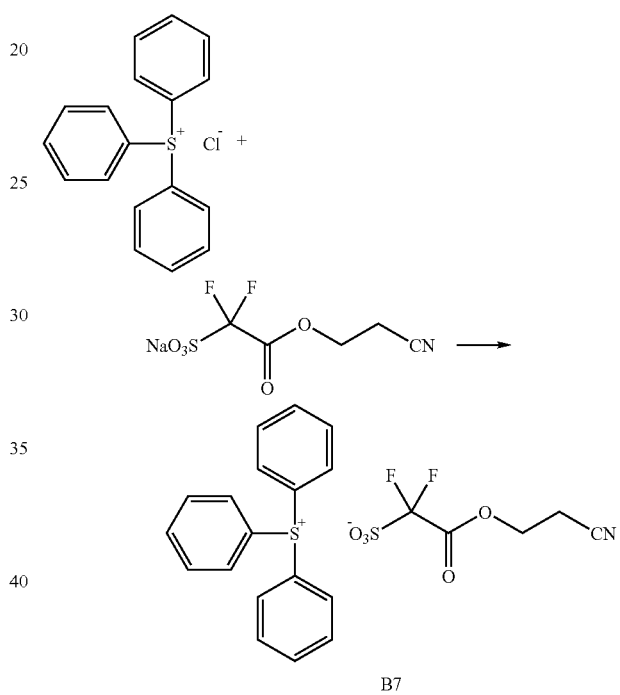

B7

H-NMR data of acid generator B7 (dimethylsulfoxide-$d_6$, Internal Standard: tetramethylsilane): d(ppm) 2.94(t, 2H); 4.41(t, 2H); 7.75-7.90(m, 15H)

MS(ESI(+) Spectrum): M+263.0 ($C_{18}H_{15}S^+$=263.09)

MS(ESI(−) Spectrum): M−228.0 ($C_5H_4F_2NO_5S^-$=227.98)

RESIN SYNTHESIS EXAMPLE 1

Synthesis of Resin A1

2-Ethyl-2-adamantyl methacrylate, 3-hydroxy-1-adamantyl methacrylate and α-methacryloyloxy-γ-butyrolactone were charged at a molar ratio of 5:2.5:2.5 (20.0 parts:9.5 parts:7.3 parts), and methyl isobutyl ketone in twice weight based on all monomers was added, to prepare solution. To the solution was added azobisisobutyronitrile as an initiator in a ratio of 2 mol % based on all monomer molar amount, and the mixture was heated at 80° C. for about 8 hours. Then, the reaction solution was poured into large amount of heptane to cause precipitation, and this operation was repeated three times for purification. As a result, copolymer having a weight-average molecular weight of about 9,200 was obtained. This is called resin A1.

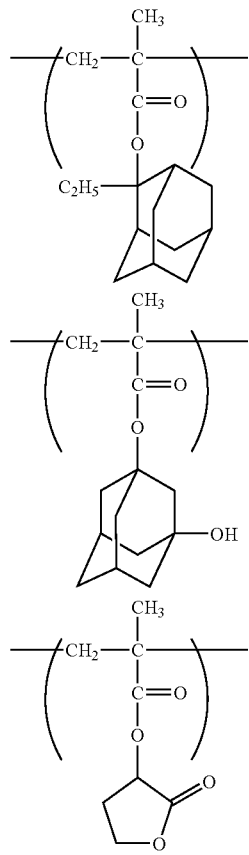

EXAMPLES 1 TO 2 AND COMPARATIVE EXAMPLE 1

The following components were mixed and dissolved, further, filtrated through a fluorine resin filter having pore diameter of 0.2 μm, to prepare resist liquid.

<Resin>
  resin A1: 10 parts

<Acid Generator>
  acid generator B1: 0.21 part

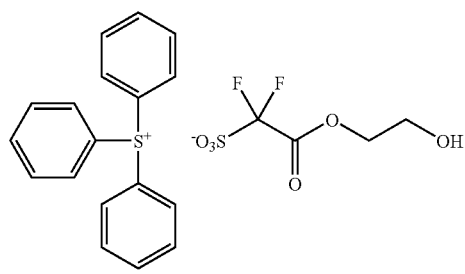

acid generator B2: 0.25 part

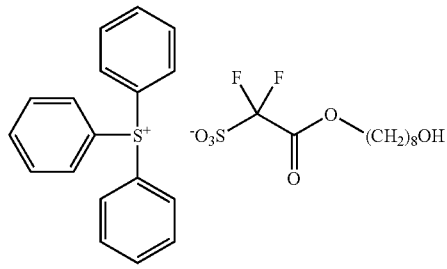

acid generator C1: 0.25 part

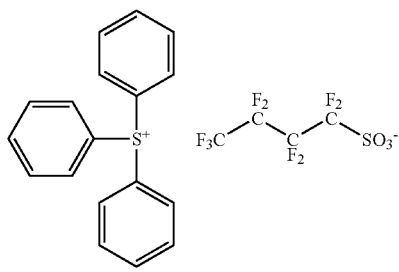

<Quencher>
  quencher Q1: 2,6-diisopropylaniline 0.0325 part

<Solvent>

| Solvent Y1: | propylene glycol monomethyl ether acetate | 80.0 parts |
| --- | --- | --- |
| | propylene glycol monomethyl ether | 20.0 parts |
| | γ-butyrolactone | 3.0 parts |

Silicon wafers were each coated with "ARC-29A-8", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.25 μm after drying. The silicon wafers thus coated with the respective resist liquids were each prebaked on a direct hotplate at a temperature of 130° C. for 60 seconds. Using an ArF excimer stepper ("NSR ArF" manufactured by Nikon Corporation, NA=0.55, ⅔Annular), each wafer thus formed with the respective resist film was subjected to line and space pattern exposure, with the exposure quantity being varied stepwise.

After the exposure, each wafer was subjected to post-exposure baking on a hotplate at a temperature of 130° C. for 60 seconds and then to paddle development for 60 seconds with an aqueous solution of 2.38 wt % tetramethylammonium hydroxide.

Each of a bright field pattern developed on the organic anti-reflective coating substrate was observed with a scanning electron microscope, the results of which are shown in Table 1. The term "bright field pattern", as used herein, means a pattern obtained by exposure and development through a reticle comprising an outer frame made of a chromium layer (light-shielding layer) and linear chromium layers (light-shielding layers) formed on a glass surface (light-transmitting portion) extending inside the outer frame. Thus, the bright field pattern is such that, after exposure and development, resist layer surrounding the line and space pattern is removed while resist layer corresponding to the outer frame is left on the outer side of the region from which the resist layer is removed.

Effective Sensitivity:

It is expressed as the amount of exposure that the line pattern (light-shielding layer) and the space pattern (light-transmitting layer) become 1:1 after exposure through 0.13 µm line and space pattern mask and development.

Resolution:

It is expressed as the minimum size of space pattern which gave the space pattern split by the line pattern at the exposure amount of the effective sensitivity.

TABLE 1

| No. | Acid Generator | Effective Sensitivity | Resolution (µm) |
|---|---|---|---|
| Example 1 | B1 | 27.5 | 0.12 |
| Example 2 | B2 | 30.0 | 0.12 |
| Comparative Example 1 | C1 | 25.0 | 0.13 |

Salt (I) is suitably used for an acid generator for chemically amplified positive resist composition. The present composition provides excellent resist pattern in resolution and is especially suitable for ArF excimer laser lithography, KrF excimer laser lithography and ArF immersion lithography.

What is claimed is:

1. A salt of the formula (I):

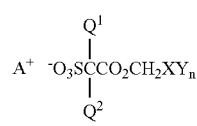

(I)

wherein X represents divalent or trivalent residue of acyclic hydrocarbon having 1 to 30 carbon atoms or divalent or trivalent residue of hydrocarbon having 3 to 30 carbon atoms which contains monocyclic or bicyclic ring, wherein —CH$_2$— in the hydrocarbon may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ each independently represent fluorine atom or perfluoroalkyl group having 1 to 6 carbon atoms; $A^+$ represents organic counter ion; Y represents hydroxyl group, cyano group or methoxy group; and n shows 1 or 2.

2. The salt according to claim 1, wherein X is divalent or trivalent residue of alkane having 1 to 30 carbon atoms, or divalent or trivalent residue of monocyclic hydrocarbon or of bicyclic hydrocarbon having 3 to 30 carbon atoms, wherein —CH$_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group.

3. The salt according to claim 2, wherein the divalent or trivalent residue of monocyclic or bicyclic hydrocarbon in X is divalent or trivalent residue of monocycloalkane or bicycloalkane.

4. The salt according to claim 1, wherein $A^+$ is at least one cation selected from the group consisting of the formula (IIe), the formula (IIb), the formula (IIc) and the formula (IId), a cation of the formula (IIe):

(IIe)

wherein $P^{25}$, $P^{26}$ and $P^{27}$ each independently represent alkyl group having 1 to 30 carbon atoms or cyclic hydrocarbon group having 3 to 30 carbon atoms, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms, a cation of the formula (IIb):

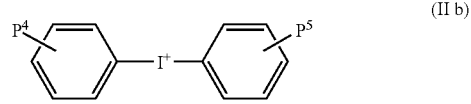

(IIb)

wherein $P^4$ and $P^5$ each independently represent hydrogen atom, hydroxyl group, alkyl group having 1 to 12 carbon atoms or alkoxy group having 1 to 12 carbon atoms, a cation of the formula (IIc):

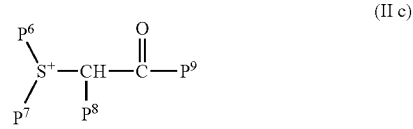

(IIc)

wherein $P^6$ and $P^7$ each independently represent alkyl having 1 to 12 carbon atoms or cycloalkyl having 3 to 12 carbon atoms, or $P^6$ and $P^7$ bond to form divalent acyclic hydrocarbon group having 3 to 12 carbon atoms which forms a ring together with the adjacent $S^+$, and one or more —CH$_2$— in the divalent acyclic hydrocarbon group is optionally substituted with —CO—, —O— or —S—, $P^8$ represents hydrogen, $P^9$ represents alkyl having 1 to 12 carbon atoms, cycloalkyl having 3 to 12 carbon atoms or aromatic ring group optionally substituted, or $P^8$ and $P^9$ bond to form divalent acyclic hydrocarbon group which forms 2-oxocycloalkyl together with the adjacent —CHCO—, and one or more —CH$_2$— in the divalent acyclic hydrocarbon group is optionally substituted with —CO—, —O— or —S—, a cation of the formula (IId):

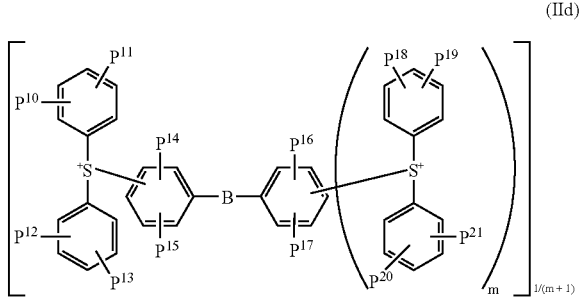

(IId)

wherein P¹⁰, P¹¹, P¹², P¹³, P¹⁴, P¹⁵, P¹⁶, P¹⁷, P¹⁸, P¹⁹, P²⁰ and P²¹ each independently represent hydrogen atom, hydroxyl group, alkyl group having 1 to 12 carbon atoms or alkoxy group having 1 to 12 carbon atoms, B represents sulfur atom or oxygen atom, and m shows 0 or 1.

5. The salt according to claim 4, wherein the cation of the formula (IIe) is a cation of the formula (IIf), (IIg) or (IIh):

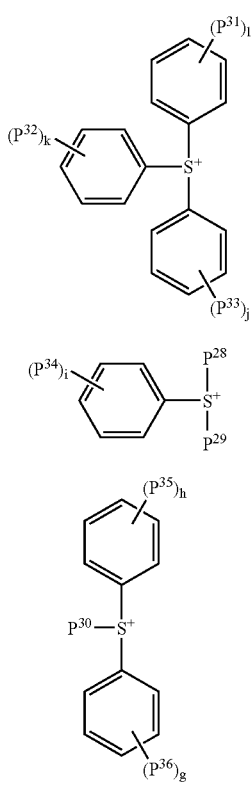

wherein P²⁸, P²⁹ and P³⁰ each independently represent alkyl group having 1 to 20 carbon atoms or cyclic hydrocarbon group having 3 to 30 except phenyl group, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms; and P³¹, P³² P³³, P³⁴, P³⁵ and P³⁶ each independently represent hydoxyl group, alkyl group having 1 to 12 carbon atoms, alkoxy group having 1 to 12 carbon atoms or cyclic hydrocarbon group having 3 to 12 carbon atoms, and l, k, j, i, h and g each independently show an integer of 0 to 5.

6. The salt according to claim 4, wherein the cation of the formula (IIe) is a cation of the formula (IIa):

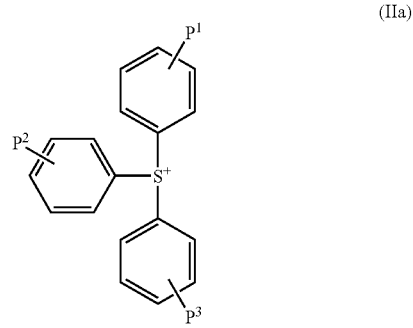

wherein P¹, P² and P³ each independently represent hydrogen atom, hydroxyl group, alkyl group having 1 to 12 carbon atoms or alkoxy group having 1 to 12 carbon atoms.

7. The salt according to claim 6, wherein the cation of the formula (IIa) is a cation of the formula (IIIe):

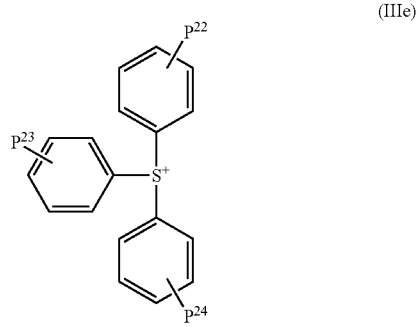

wherein P²², P²³ and P²⁴ each independently represent hydrogen atom or alkyl group having 1 to 4 atoms.

8. The salt according to claim 1, wherein each of Q¹ and Q² is independently fluorine atom or trifluoromethyl group.

9. The salt according to claim 2, wherein X is divalent or trivalent residue of alkane having 1 to 30 carbon atoms, of cycloalkane having 3 to 10 carbon atoms or of norbornane, wherein —CH₂— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; Q¹ and Q² are both fluorine atoms; Y is hydroxyl group; and n shows 1.

10. The salt according to claim 1, wherein the salt is the one of the formula (IIIa), (IIIb) or (IIIc);

(IIIa)

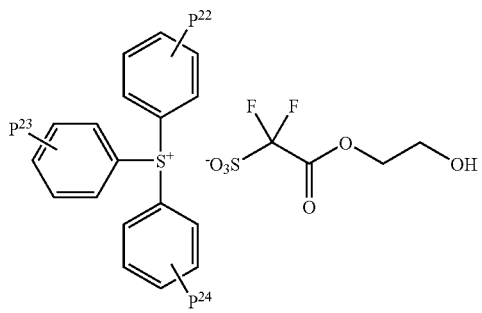

(IIIb)

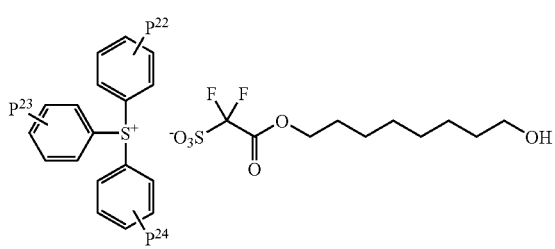

(IIIc)

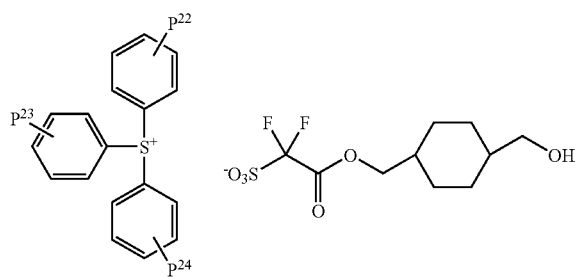

wherein P²², P²³ and P²⁴ have the same meanings as defined in claim 7.

11. A process for producing a salt of the formula (I)

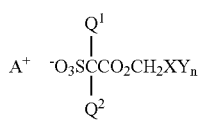 (I)

wherein X represents divalent or trivalent residue of acyclic hydrocarbon having 1 to 30 carbon atoms or divalent or trivalent residue of hydrocarbon having 3 to 30 carbon atoms which contains monocyclic or bicyclic ring, wherein —CH$_2$— in the hydrocarbon may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; Q$^1$ and Q$^2$ each independently represent fluorine atom or perfluoroalkyl group having 1 to 6 carbon atoms; A$^+$ represents organic counter ion; Y represents hydroxyl group, cyano group or methoxy group; and n shows 1 or 2, which comprises reacting an ester compound of the formula (IV)

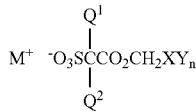 (IV)

wherein M represents Li, Na, K or Ag, and X, Y, Q$^1$, Q$^2$ and n have the same meanings as defined above,
with a compound of the formula (VII)

$$A^+Z^-$$ (VII)

wherein Z represents F, Cl, Br, I, BF$_4$, AsF$_6$, PF$_6$ or ClO$_4$, and A$^+$ has the same meaning as defined above.

12. A chemically amplified resist composition comprising a salt of the formula (1)

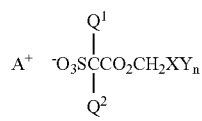 (I)

wherein X represents divalent or trivalent residue of acyclic hydrocarbon having 1 to 30 carbon atoms or divalent or trivalent residue of hydrocarbon having 3 to 30 carbon atoms which contains monocyclic or bicyclic ring, wherein —CH$_2$— in the hydrocarbon may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; Q$^1$ and Q$^2$ each independently represent fluorine atom or perfluoroalkyl group having 1 to 6 carbon atoms; A$^+$ represents organic counter ion; Y represents hydroxyl group, cyano group or methoxy group; and n shows 1 or 2, and
a resin which contains a structural unit having an acid-labile group and which itself is insoluble or poorly soluble in an alkali aqueous solution but becomes soluble in an alkali aqueous solution by the action of an acid.

13. The composition according to claim 12, wherein each of Q$^1$ and Q$^2$ is independently fluorine atom or trifluoromethyl group.

14. The composition according to claim 12, wherein the resin contains a structural unit derived from a monomer having a bulky and acid-labile group.

15. The composition according to claim 14, wherein the bulky and acid-labile group is 2-alkyl-2-adamantyl group or 1-(1-adamantyl)-1-alkylalkyl group.

16. The composition according to claim 14, wherein the monomer having bulky and acid-labile group is 2-alkyl-2-adamantyl (meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

17. The composition according to claim 12, wherein the composition further comprises a basic compound.

18. The composition according to claim 12, wherein X is divalent or trivalent residue of alkane having 1 to 30 carbon atoms, or divalent or trivalent residue of monocyclic hydrocarbon or of bicyclic hydrocarbon having 3 to 30 carbon atoms, wherein —CH$_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group.

19. The composition according to claim 18, wherein the divalent or trivalent residue of monocyclic or bicyclic hydrocarbon in X is divalent or trivalent residue of monocycloalkane or bicycloalkane.

20. The composition according to claim 12, wherein A$^+$ is at least one cation selected from the group consisting of the formula (IIe), the formula (IIb), the formula (IIc) and the formula (IId),

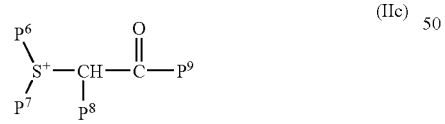
(IIe)

wherein P$^{25}$, P$^{26}$ and P$^{27}$ each independently represent alkyl group having 1 to 30 carbon atoms or cyclic hydrocarbon group having 3 to 30 carbon atoms, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms, a cation of the formula (IIb):

(IIb)

wherein P$^4$ and P$^5$ each independently represent hydrogen atom, hydroxyl group, alkyl group having 1 to 12 carbon atoms or alkoxy group having 1 to 12 carbon atoms, a cation of the formula (IIc):

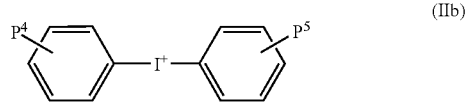
(IIc)

wherein P$^6$ and P$^7$ each independently represent alkyl having 1 to 12 carbon atoms or cycloalkyl having 3 to 12 carbon atoms, or P$^6$ and P$^7$ bond to form divalent acyclic hydrocarbon group having 3 to 12 carbon atoms which forms a ring together with the adjacent S$^+$, and one or more —CH$_2$— in the divalent acyclic hydrocarbon group is optionally substituted with —CO—, —O— or —S—, P$^8$ represents hydrogen, P$^9$ represents alkyl having 1 to 12 carbon atoms, cycloalkyl having 3 to 12 carbon atoms or aromatic ring group optionally substituted, or P$^8$ and P$^9$ bond to form divalent acyclic hydrocarbon group which forms 2-oxocycloalkyl together with the adjacent —CHCO—, and one or more —CH$_2$— in the divalent acyclic hydrocarbon group is optionally substituted with —CO—, —O— or —S—, a cation of the formula (IId):

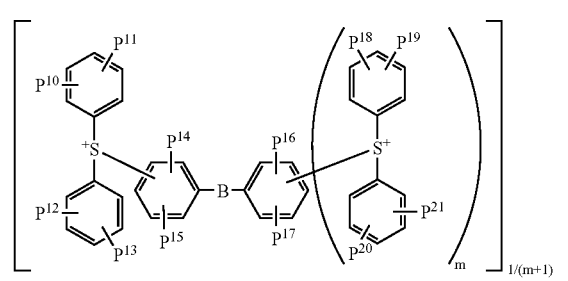
(IId)

wherein P$^{10}$, P$^{11}$, P$^{12}$, P$^{13}$, P$^{14}$, P$^{15}$, P$^{16}$, P$^{17}$, P$^{18}$, P$^{19}$, P$^{20}$ and P$^{21}$ each independently represent hydrogen atom, hydroxyl group, alkyl group having 1 to 12 carbon atoms or alkoxy group having 1 to 12 carbon atoms, B represents sulfur atom or oxygen atom, and m shows 0 or 1.

21. The composition according to claim 20, wherein the cation of the formula (IIe) is a cation of the formula (IIf), (IIg) or (IIh):

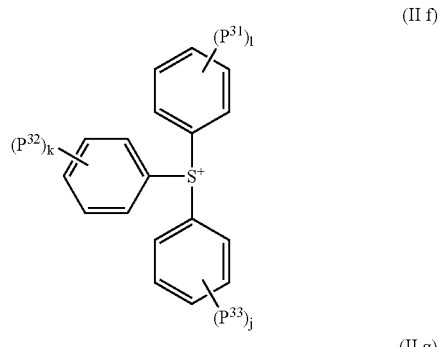
(IIf)

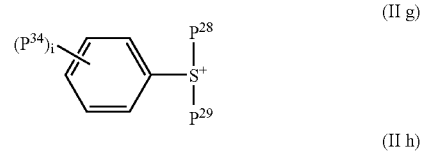
(IIg)

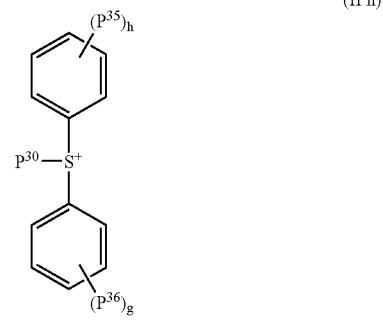
(IIh)

wherein P$^{28}$, P$^{29}$ and P$^{30}$ each independently represent alkyl group having 1 to 20 carbon atoms or cyclic hydrocarbon group having 3 to 30 except phenyl group, wherein one or more hydrogen atom in the alkyl group is optionally substituted with hydroxyl group, alkoxy group having 1 to 12 carbon atoms or cyclic hydrocarbon group having 3 to 12 carbon atoms and wherein one or more hydrogen atom in the cyclic hydrocarbon group is optionally substituted with hydroxyl group, alkyl group having 1 to 12 carbon atoms or alkoxy group having 1 to 12 carbon atoms; and $P^{31}$, $P^{32}$, $P^{33}$, $P^{34}$, $P^{35}$ and $P^{36}$ each independently represent hydoxyl group, alkyl group having 1 to 12 carbon atoms, alkoxy group having 1 to 12 carbon atoms or cyclic hydrocarbon group having 3 to 12 carbon atoms, and l, k, j, i, h and g each independently show an integer of 0 to 5.

22. The composition according to claim 20, wherein the cation of the formula (IIe) is a cation of the formula (IIa):

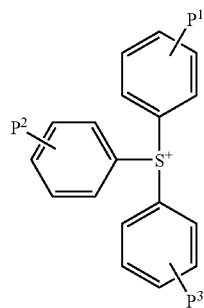

(IIa)

wherein $P^1$, $P^2$ and $P^3$ each independently represent hydrogen atom, hydroxyl group, alkyl group having 1 to 12 carbon atoms or alkoxy group having 1 to 12 carbon atoms.

23. The composition according to claim 22, wherein the cation of the formula (IIa) is a cation of the formula (IIIe):

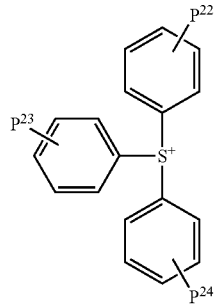

(IIIe)

wherein $P^{22}$, $P^{23}$ and $P^{24}$ each independently represent hydrogen atom or alkyl group having 1 to 4 atoms.

24. The composition according to claim 18, wherein X is divalent or trivalent residue of alkane having 1 to 30 carbon atoms, of cycloalkane having 3 to 10 carbon atoms or of norbornane, wherein —$CH_2$— in the alkane may be substituted with —O— and one or more hydrogen atom in X is optionally substituted with alkoxy group having 1 to 6 carbon atoms, perfluoroalkyl group having 1 to 4 carbon atoms, hydroxyalkyl group having 1 to 6 carbon atoms, hydroxyl group or cyano group; $Q^1$ and $Q^2$ are both fluorine atoms; Y is hydroxyl group; and n shows 1.

25. The composition according to claim 12, wherein the salt is the one of the formula (IIIa), (IIIb) or (IIIc);

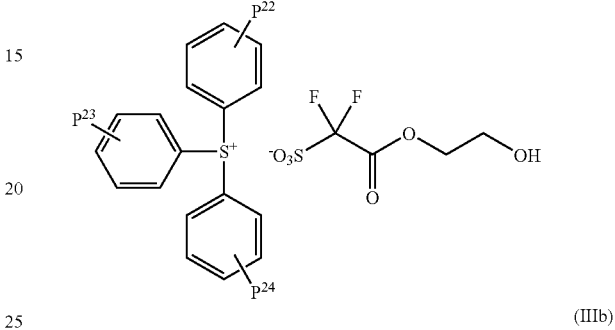

(IIIa)

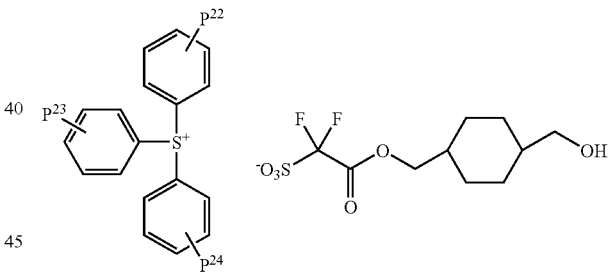

(IIIb)

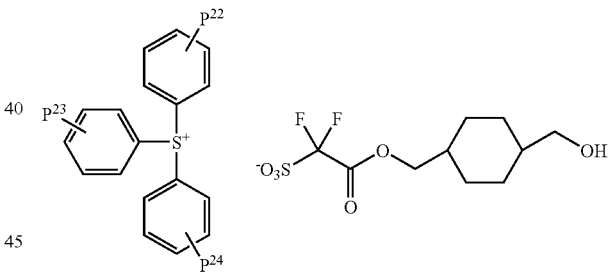

(IIIc)

wherein $P^{22}$, $P^{23}$ and $P^{24}$ have the same meanings as defined in claim 23.

* * * * *